United States Patent [19]

Hirai et al.

[11] Patent Number: 4,882,338
[45] Date of Patent: Nov. 21, 1989

[54] SUBSTITUTED ISOQUINOLINE DERIVATIVES AND ANTI-ULCER AGENTS

[75] Inventors: Kentaro Hirai, Kyoto; Yukio Mizushima, Osaka, both of Japan

[73] Assignee: Shionogi & Co., Ltd., Osaka, Japan

[21] Appl. No.: 68,934

[22] Filed: Jul. 1, 1987

[30] Foreign Application Priority Data

Jul. 1, 1986 [JP] Japan .................. 61-155412

[51] Int. Cl.$^4$ .................. A61K 31/47; C07D 401/12; C07D 405/14
[52] U.S. Cl. .................. 514/307; 514/291; 546/90; 546/146; 546/147; 546/148
[58] Field of Search .................. 546/148, 147, 90; 514/307, 291

[56] References Cited

FOREIGN PATENT DOCUMENTS 2134523 8/1984 United Kingdom .
2174988 5/1986 United Kingdom .

OTHER PUBLICATIONS

Braendstroem, et al., "Chemical Abstracts," vol. 101, 1984, Col. 101:230546r.
Hirai, et al., "Chemical Abstracts," vol. 108, 1988, Col. 108:167471q.

Primary Examiner—Glennon H. Hollrah
Assistant Examiner—James H. Turnipseed

Attorney, Agent, or Firm—Birch, Stewart, Kolasch & Birch

[57] ABSTRACT

A compound of the formula:

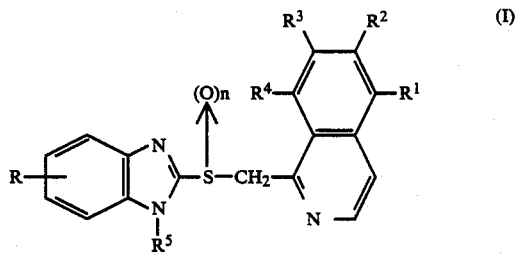

(wherein R is hydrogen, hydroxy, methoxy, acetoxy, acetoxymethyl or trifluoromethyl;

$R^1$, $R^2$, $R^3$ and $R^4$ each is hydrogen, hydroxy, optionally substituted $C_1$-$C_5$ alkoxy, acetoxy, propynyloxy, allyloxy or benzyloxy; or $R^2$ and $R^3$ taken together form methylenedioxy;

$R^5$ is hydrogen, hydroxymethyl, $C_2$-$C_4$ alkoxycarbonyl, $C_2$-$C_5$ acyloxymethyl or phthalidyl; and n is 0 or 1 except for the case in which R is methoxy and $R^1$, $R^2$, $R^3$, $R^4$ and $R^5$ each is hydrogen) or its pharmaceutically acceptable acid addition salt, being useful as anti-ulcer agents is provided through several routes.

21 Claims, No Drawings

SUBSTITUTED ISOQUINOLINE DERIVATIVES AND ANTI-ULCER AGENTS

The present invention relates to substituted isoquinoline derivatives. More particularly, this invention is directed to substituted isoquinoline derivatives which have been found to be particularly effective in the treatment of an ulcer, to their production, to their use and to pharmaceutical formulations containing the compounds.

2-[(1-Isoquinolylmethyl)sulfinyl]-5-methoxybenzimidazole is hitherto known as this kind of compound, but this compound is defectively somewhat low in the acid secretion-suppressing action (Brit. Pat. No. 2134523-A).

The inventors of the present inventions have been studying anti-ulcer agents of benzimidazole family.

According to the present invention there is provided a substituted isoquinoline derivative of the formula:

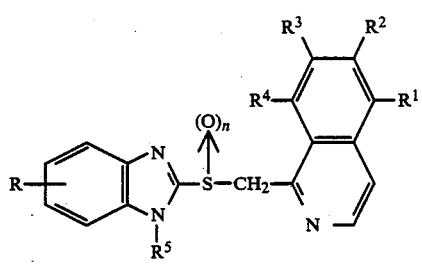

(wherein R is hydrogen, hydroxy, methoxy, acetoxy, acetoxymethyl or trifluoromethyl;
$R^1$, $R^2$, $R^3$ and $R^4$ each is hydrogen, hydroxy, optionally substituted $C_1$-$C_5$ alkoxy, propynyloxy, allyloxy or benzyloxy; or $R^2$ and $R^3$ taken together form methylenedioxy;
$R^5$ is hydrogen, hydroxymethyl, $C_2$-$C_4$ alkoxycarbonyl, $C_2$-$C_5$ acyloxymethyl or phthalidyl;
and n is 0 or 1 except for the case in which R is methoxy and $R^1$, $R^2$, $R^3$, $R^4$ and $R^5$ each is hydrogen) or its pharmaceutically acceptable acid addition salt.

The compounds of the present invention have an excellent anti-ulcer activity. Accordingly the invention also provides a pharmaceutical composition as an active ingredient 0.1 to 95% by weight of at least a compound of the formula (I) associated with at least one carrier, diluent and/or excipient therefor.

This invention also provides a method of treating a patient suffering from an ulcer which comprises administering to the patient a pharmacologically effective amount of a compound of the formula (I).

This invention further provides a process for preparing a compound of the formula (I) which comprises:

(a) reacting a compound of the formula:

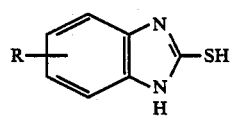

(wherein R is as defined above)
with a compound of the formula:

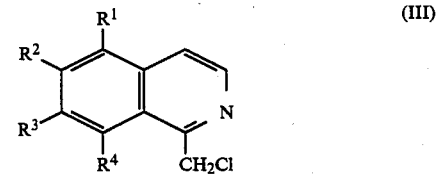

or

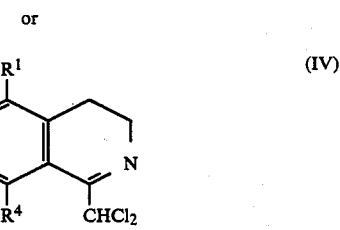

(wherein $R^1$, $R^2$, $R^3$ and $R^4$ each has the same meaning as defined above)
to give a compound of the formula:

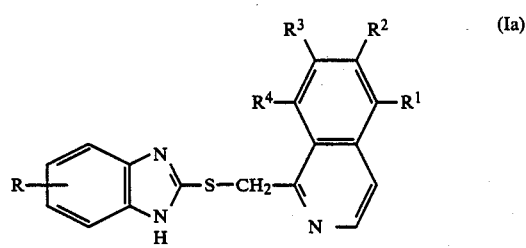

(wherein R, $R^1$, $R^2$, $R^3$ and $R^4$ each has the same meaning as defined above), (b) subjecting the compound (Ia) to (i) hydroxymethylation followed by O-acylation of (ii) N-substitution with halomethyl alkanoate or 3-halophthalide to give a compound of the formula:

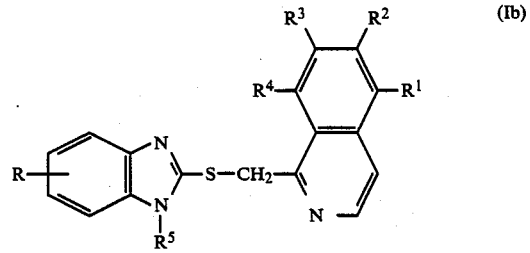

(wherein R, $R^1$, $R^2$, $R^3$, $R^4$ and $R^5$ each has the same meaning as defined above), (c) oxidizing the compound (Ia) to give a compound of the formula:

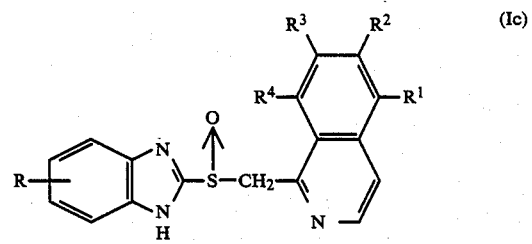

(wherein R, $R^1$, $R^2$, $R^3$ and $R^4$ each has the same meaning as defined above), (d) oxidizing the compound (Ib) to give a compound of the formula:

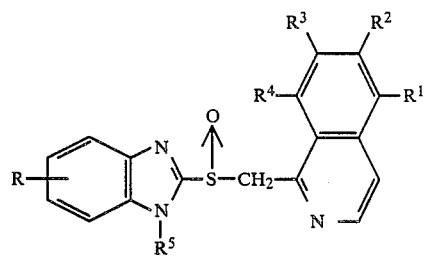

(wherein R, $R^1$, $R^2$, $R^3$ and $R^4$ each has the same meaning as defined above and $R^5$ is $C_2$-$C_5$ acyloxymethyl or phthalidyl).

The term "$C_1$-$C_5$ alkoxy" represent methoxy, ethoxy, n-propoxy, iso-propoxy, n-butoxy, iso-butoxy, sec-butoxy, tert-butoxy, n-pentyloxy, iso-pentyloxy, sec-pentyloxy, neo-pentyloxy, or tert-pentyloxy. The optical substitutent on the $C_1$-$C_5$ alkoxy includes $C_3$-$C_6$ cycloalkyl such as cyclopropyl, cyclopentyl or cyclohexyl and one or more halogens such as fluorine, chlorine or bromine.

The term "$C_2$-$C_4$ alkoxycarbonyl" includes ethoxycarbonyl, propoxycarbonyl, butoxycarbonyl and isobutoxycarbonyl.

The term "$C_2$-$C_5$ acyloxymethyl" includes alkanoyloxymethyl (e.g. acetoxymethyl, propionyloxymethyl, butyryloxymethyl, pivaloyloxymethyl, valeryloxymethyl) and alkoxycarbonyloxymethyl (e.g. ethoxycarbonyloxymethyl, propoxycarbonyloxymethyl, butoxycarbonyloxymethyl).

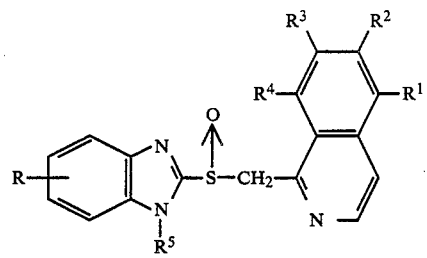

(wherein R, $R^1$, $R^2$, $R^3$ and $R^4$ each has the same meaning as defined above and $R^5$ is $C_2$-$C_4$ alkoxycarbonyl, $C_2$-$C_5$ acyloxymethyl or phthalidyl), or (e) subjecting the compound (Ic) to N-substitution with halomethyl alkanoate or 3-halophthalide to give a compound of the formula:

The process for preparing the compound (I) is shown by the scheme as follows:

Step I

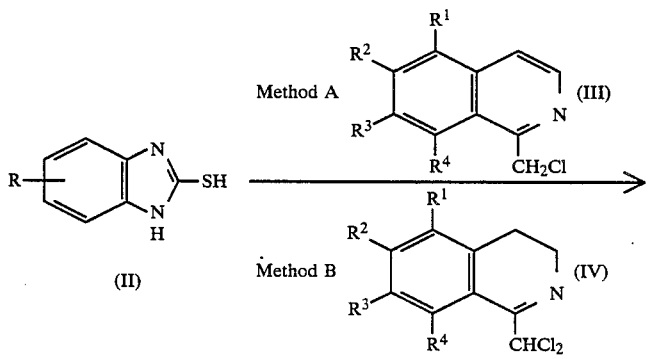

Step II

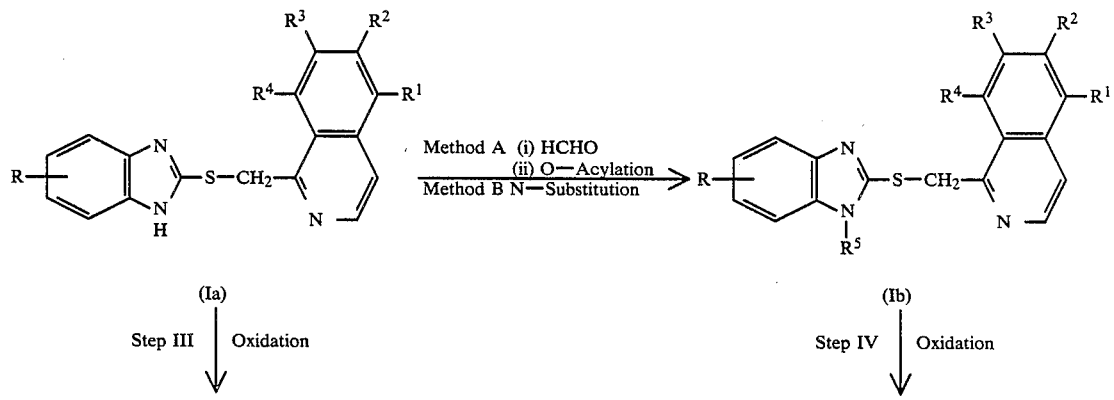

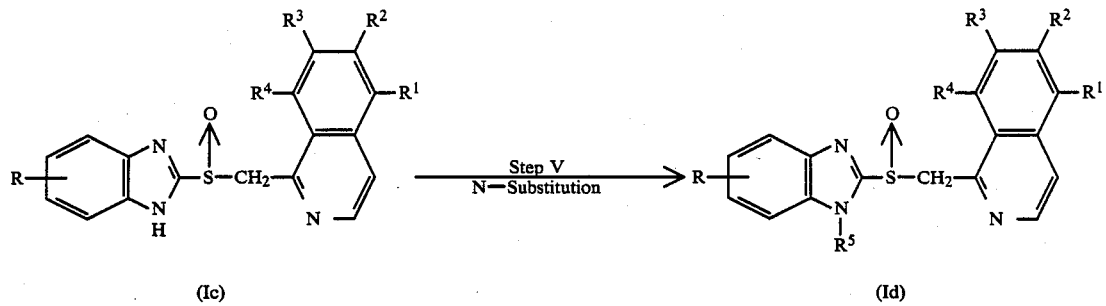

(wherein R, $R^1$, $R^2$, $R^3$, $R^4$ and $R^5$ each has the same meaning as defined above).

STEP I

Method A

In this step, the compound (II) is allowed to react with the compound (III) in the presence of a base in an appropriate solvent, whereby the objective compound (Ia) is obtained.

As the base used in this reaction, an inorganic base (e.g. $K_2CO_3$, $Na_2CO_3$, NaOH, $NaHCO_3$, etc.) and an organic base (e.g. $Et_3N$, pyridine, etc.) are exemplified.

As the solvent MeOH, EtOH, benzene, $CHCl_3$, carbon tetrachloride, dimethyl sulfoxide, tetrahydrofuran, dimethylformamide and water are exemplified.

The reaction was performed at 0°–120° C., preferably 15°–50° C.

Method B

In this step, the compound (II) is allowed to react with the compound (IV) to give the objective compound (Ia) as in Method A.

This reaction is peformed by using the said base and solvent at 15°–120° C., but it is preferable to use the KOH-EtOH system with heating up to a reflux temperature of the solvent.

In this reaction the aromatization of the dihydroquinoline ring by dehydrogenation brings about at the same time, whereby the objective compound (Ia) is obtained in a good yield.

STEP II

Method A

The compound (Ia) obtained in the former step is allowed to react with formaldehyde in a solvent such as acetonitrile or dimethylformamide to give the compound (Ib) ($R^5$=CH$_2$OH). This hydroxymethylation is performed at 15°–100° C., preferably at 50°–80° C.

Then, the compound (Ib) ($R^5$=CH$_2$OH) is subjected to acylation to produce the O-acylate (Ib) containing the $R^5$ moiety.

This reaction is performed by using an acid anhydride (e.g. acetic anhydride, butyric anhydride, etc.) or lower alkyl haloformate (e.g. ethyl chloroformate, n-propyl chloroformate, etc.). If necessary, it can be carried out in a conventional manner for acylation in the presence of a solvent and/or a base as illustrated above. The reaction is performed at 15° to 120° C., preferably 50° to 100° C.

In the case of using lower alkyl haloformate as an acylating agent, eventually the N-alkoxycarbonyl compound (Ib) ($R^5$=alkoxycarbonyl) is produced together with the N-acyloxymethyl compound (Ib) ($R^5$=alkoxycarbonyloxymethyl).

Method B

Alternatively, the compound (Ia) is subjected to N-substitution to give the N-substituted compound (Ib) ($R^5$=alkanoyloxymethyl or phthalidyl). The compound (Ia) is allowed to react with halomethyl alkanoate (e.g. chloromethyl pivalate, bromomethyl butyrate, chloromethyl acetate, etc.) or 3-halophthalide (e.g. 3-chlorophthalide, 3-bromophthalide).

The reaction with halomethyl alkanoate is performed in the presence of a base such as alkali metal hydride (e.g. sodium hydride) or potassium hydride in a solvent such as dimethylformamide, hexamethylphosphoramide or the like at 15° to 100° C., preferably at room temperature.

Further, the reaction with 3-halophthalide is performed in the presence of a base such as sodium hydride or triethylamine in a solvent such as dimethylformamide, hexamethylphosphoramide or the like at 15° to 120° C., preferably at 50° to 80° C.

STEP III

The compound of (Ia) is oxidized with a peracid to give the sulfinyl compound (Ic). The oxidation is performed with appropriate oxidizing agents (e.g. hydrogen peroxide, perbenzoic acid, m-chloroperbenzoic acid or the like) in a solvent such as chloroform, 1,2-dichloroethane, carbon tetrachloride, dimethylformamide, acetic acid or the like at a temperature from −100° to 0° C., preferably −30° to −5° C., or at room temperature (e.g. 15° to 25° C.). After finishing the reaction, the mixture is treated with aqueous sodium bisulfite for decomposing a certain amount of the peracid remaining there in a conventional manner.

STEP IV

The compound (Ib) is oxidized with a peracid to give the sulfinyl compound (Id). This oxidation is performed under the same conditions as in Step III.

STEP V

The compound (Ic) is subjected to N-substitution with halomethyl alkanoate or 3-halophthalide to give the N-substitution compound (Id). The N-substitution is performed under the same conditions as in Method B of Step II.

The starting material (III) and (IV), for example, can be manufactured by the following process.

Preparation of Compound (III)

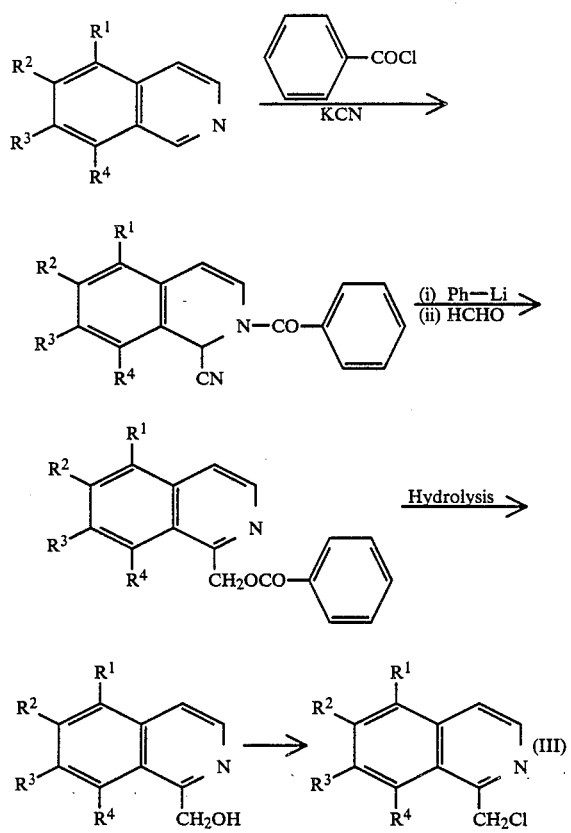

(wherein $R^1$, $R^2$, $R^3$ and $R^4$ each has the same meaning as defined above).
[Ref: Gibson et al., J. Heterocyclic Chem., 1 251 (1964)]

Preparation of Compound (IV)

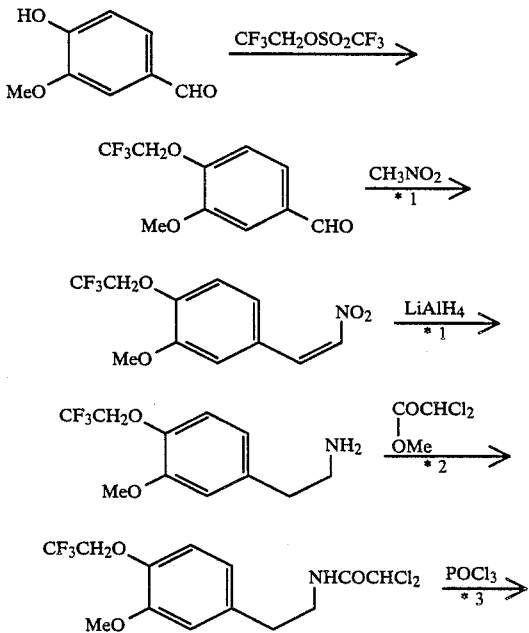

-continued
Preparation of Compound (IV)

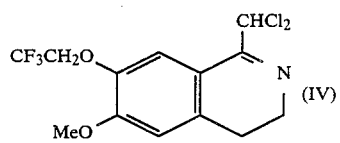

* 1: M. F. Grundon et al., J. Chem. Soc., 3531 (1954)
* 2: A. P. Phillips, J. Am. Chem. Soc., 74 6125 (1952)
* 3: D. Pawellek et al., J. Org. Chem., 25 281 (1960)

The compound (I) can be converted into its pharmaceutically acceptable acid addition salts. Such acids illustratively include an inorganic acid such as hydrochloric acid, sulfuric acid, phosphoric acid or nitric acid and an organic acid such as acetic acid, maleic acid, malic acid, citric acid, lactic acid, succinic or methanesulfonic acid.

The compounds (I) can be administered enterally or parenterally to human being. They can be formulated as tablets, capsules, pills, granules, injections, suppositories and syrups according to customary pharmaceutical practice. As pharmaceutically acceptable carriers, diluents or excipients, there are examplified lactose, sucrose, wheat starch, potato starch, magnesium stearate, gelatin, methyl cellulose, agar, water and the like. A necessary, appropriate stabilizers, emulsifiers, spreaders, buffers and other pharmaceutical adjuvants can be added. Appropriate daily dosage of the compound (I) is 0.1 to 500 mg in oral route and 0.1 to 3000 mg in injection.

The present invention will be explained in more detail by the following Examples, Reference Examples and Formulations.

The abbreviations used in the Examples, Reference Examples and Tables are as follows.
Me: methyl
Ph: phenyl
EtOH: ethanol
AcOH: acetic acid
$CH_3CN$: acetonitrile
$Et_2O$: ethylether
$CH_2Cl_2$: dichloromethane
$CHCl_3$: chloroform
THF: tetrahydrofuran
DMF: dimethylformamide
$POCl_3$: phosphorus oxychloride
$LiAlH_4$: lithium alminium hydride
MeO: methoxy
EtO: ethoxy
O-Al: allyloxy
O-Bz: benzyloxy
O-i-Pro: isopropyloxy
(d): decomposition
Et: ethyl
MeOH: methanol
KOH: potassium hydroxide
NaOH: sodium hydroxide
KCN: potassium cyanide
AcOEt: ethyl acetate
HCHO: formaldehyde
$Et_3N$: triethylamine
NaH: sodium hydride.

EXAMPLE 1

2-[(6,7-Dimethoxyisoquinolin-1-yl)methyltho]benzimidazole (Ia-1)

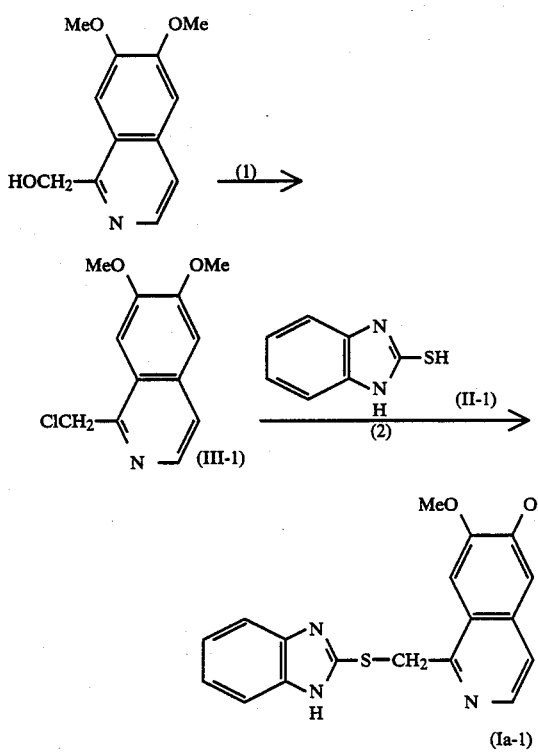

(1) To 306.3 mg of 6,7-dimethoxyisoquinolin-1-ylmethanol (1.397 mmol) were added 20 ml of dry CH$_2$Cl$_2$ and 665 mg of thionyl chloride (5.95 mmol) and the mixture was stirred for 2 hours at room temperature. The reaction solution was concentrated to give 490mg of 1-chloro-(6,7-dimethoxyisoquinolin-1-yl)methane (III-1) as brown crystals.

(2) To the above product were added 220.3 mg of 2-mercaptobenzimidazole (1.467 mmol), 1.16 g of potassium carbonate (8.38 mmol) and 10 ml of dry dimethylformamide, and the mixture was stirred for 17 hours at room temperature. Dimethylformamide was distilled off under reduced pressure. Water was added to the residue and the mixture was extracted with CH$_2$Cl$_2$. The organic layer was dried over anhydrous sodium sulfate and concentrated under reduced pressure. The residue was subjected to silica gel column chromatography for purification. The extract was crystallized from CH$_2$Cl$_2$-cyclohexane to give 369.1 mg of the objective compound 2-[(6,7-dimethoxy-isoquinolin-1-yl)methylthio]benzimidazole (Ia-1) (yield: 75.2%) as crystals.

m.p.: 183.5°–185.5° C. (d).

Anal Calcd. (%) for C$_{19}$H$_{17}$N$_3$O$_2$S: C, 64.74; H, 4.88; N, 11.96; S, 9.12. Found (%): C, 64.82; H, 4.77; N, 11.86; S, 9.15.

EXAMPLE 2-6

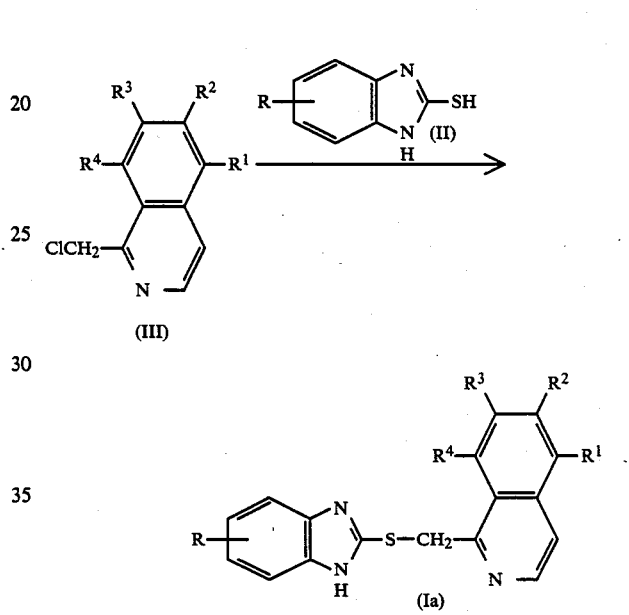

(wherein R$^1$, R$^2$, R$^3$, R$^4$ and R have the same meaning as defined above).

In the same method as in Example 1, the reaction was performed under the reaction conditions as defined in Table 1, whereby the objective compounds (Ia) were obtained.

TABLE 1

| Ex. No. | R¹ | R² | R³ | R⁴ | R | Compd. (II-1) ml (mmol) | Compd. (III) mg (mmol) | Yield mg/(%) | Compd. (Ia) No. | m.p. (°C.) | Molecular Formula | Elemental Analysis (%) up: Calcd. down: Found ||||| 
|---|---|---|---|---|---|---|---|---|---|---|---|---|---|---|---|---|
| | | | | | | | | | | | | C | H | N | S | F |
| 2 | H | H | OMe | H | H | 296.3 (1.973) | 355.5 (1.879) | 452.1 (74.9) | Ia-2 | 201.0–203.0 (d) | $C_{18}H_{15}N_3OS$ | 67.27 67.20 | 4.70 4.72 | 13.07 13.09 | 9.98 10.21 | |
| 3 | H | OMe | OMe | H | 5-CF₃ | 376.6 (1.726) | 360.4 (1.644) | 595.2 (85.1) | Ia-3 | 229.0–232.0 (d) | $C_{20}H_{16}N_3O_2SF \cdot \tfrac{1}{4}H_2O$ | 56.47 56.49 | 3.95 3.91 | 9.88 9.79 | 7.54 7.83 | 13.40 13.02 |
| 4 | H | OMe | OMe | H | 5-OMe | 311.1 (1.726) | 360.4 (1.644) | 442.1 (70.2) | Ia-4 | 183.0–184.5 (d) | $C_{20}H_{19}N_3O_3S \cdot 1/10H_2O$ | 62.68 62.66 | 5.05 5.12 | 10.96 11.07 | 8.36 8.34 | |
| 5 | OMe | OMe | OMe | H | H | 248.6 (1.655) | 392.8 (1.576) | 455.3 (75.0) | Ia-5 | 190.5–192.0 (d) | $C_{20}H_{19}N_3O_3S \cdot 1/5H_2O$ | 62.39 62.43 | 4.97 5.01 | 10.91 10.95 | 8.33 8.33 | |
| 6 | H | —OCH₂O— | | H | H | 235.1 (1.565) | 302.8 (1.490) | 308.0 (61.6) | Ia-6 | 214.0–216.0 (d) | $C_{18}H_{13}N_3O_2S$ | 64.46 64.32 | 3.91 3.97 | 12.53 12.34 | 9.56 9.80 | |

EXAMPLE 7

2-{[6-Methoxy-7-(2,2,2-trifluoroethoxy)isoquinolin-1-yl]-methylthio}benzimidazole (Ia-7)

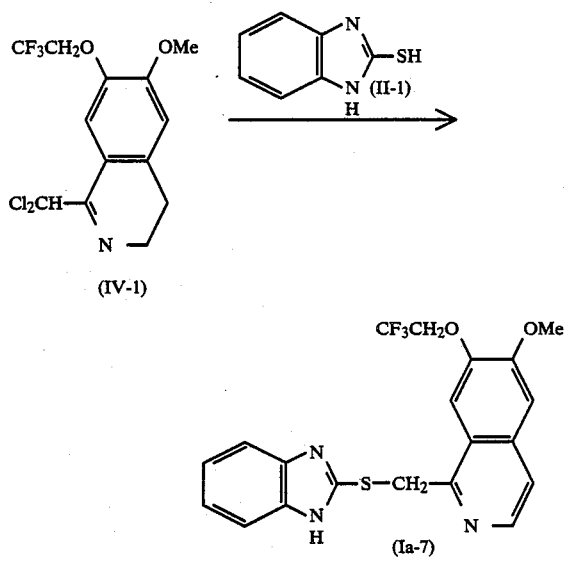

To a solution of 514.8 mg of 86% KOH (7.87 mmol) in 20 ml of 99% EtOH were added 434.1 mg of 2-mercaptobenzimidazole (II-1) (2.89 mmol) and 900.1 mg of 1-dichloromethyl-6-methoxy-7-(2,2,2-trifluoroethoxy)-3,4-dihydroisoquinoline (IV-1) (2.63 mmol) in order. After stirring for 30 min. at room temperature, the mixture was refluxed for 3 hr. and concentrated under reduced pressure. The residue was mixed with water and extracted with CHCl$_3$. The objective compound existing as an insoluble material was filtered and combined with CHCl$_3$ extract to give 722.5 mg of the crude product. It was dispersed in 15 ml of CH$_2$Cl$_2$, filtered and washed with CH$_2$Cl$_2$ to give 666.5 mg of the titled compound 2-{[6-methoxy-7-(2,2,2-trifluoroethoxy)isoquinolin-1-yl]methylthio}-benzimidazole (Ia-7) (Yield: 60.4%).

m.p.: 232°–234° C. (d).

Anal. Calcd. (%) for $C_{20}H_{16}N_3O_2SF_3$: C, 57.27; H, 3.84; N, 10.02; S, 7.64; F, 13.59. Found (%): C, 56.98; H, 392; N, 9.97; S, 7.77; F, 13.36.

EXAMPLE 8–21

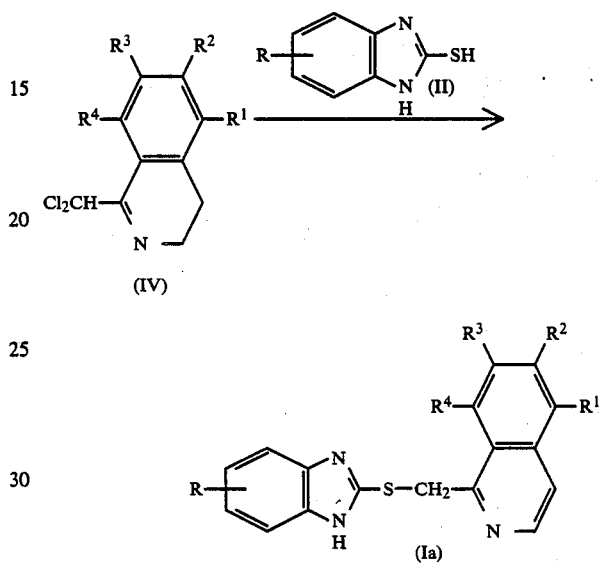

(wherein $R^1$, $R^2$, $R^3$ and $R^4$ have the same meaning as defined above).

In the same method as in Example 7, the reaction was performed under the reaction conditions as defined in Table 2, whereby the objectivecompounds (Ia) were obtained.

TABLE 2

(No. 1)

| Ex. No. | R¹ | R² | R³ | R⁴ | R | EtOH (ml) | KOH (mg) | Compd. (II-1) (mg) | Compd. (IV) (mg) | Compd. (Ia) No. | Yield (mg) (%) | m.p. (°C.) | Molecular Formula | Elemental Analysis (%) up: Calcd. down: Found C | H | N | S | F |
|---|---|---|---|---|---|---|---|---|---|---|---|---|---|---|---|---|---|---|
| 8 | H | OCH₂CF₃ | OMe | H | H | 20 | 678.5 | 570.8 | 1180 | Ia-8 | 1030 (71.2) | 188-192 (d) | C₂₀H₁₆N₃O₂SF₃ | 57.27 57.37 | 3.84 4.01 | 10.02 9.87 | 7.64 7.86 | 13.59 13.36 |
| 9 | H | OCH₂CF₃ | OCH₂CF₃ | H | H | 3 | 111.6 | 94.3 | 234 | Ia-9 | 163 (57.2) | 205-208 (d) | C₂₁H₁₆N₃O₂SF₆·½H₂O | 50.50 50.54 | 3.30 3.13 | 8.41 8.34 | 6.42 6.64 | 22.82 22.16 |
| 10 | H | O—Al | OMe | H | H | 20 | 650.0 | 1000 | 500 | Ia-10 | 740 (58.7) | 183-185 | C₂₁H₁₉N₃O₂ | 66.82 66.94 | 5.07 5.09 | 11.13 11.07 | 8.49 8.77 | — |
| 11 | H | O—Al | H | H | H | 10 | 270.0 | 370 | 210 | Ia-11 | 180 (37.5) | 175-176 | C₂₀H₁₇N₃O₂ | 69.14 69.41 | 4.93 4.99 | 12.09 11.82 | 9.23 9.02 | — |
| 12 | H | OMe | H | H | H | 15 | 340.0 | 430 | 260 | Ia-12 | 240 (43.2) | 192-199 (d) | C₁₈H₁₆N₃SO | 67.27 67.05 | 4.70 4.79 | 13.07 12.78 | 9.98 9.72 | — |
| 13 | H | OMe | OMe | H | H | 20 | 690.0 | 960 | 530 | Ia-13 | 720 (67.7) | 183.5-185.5 (d) | C₁₉H₁₇N₃O₂S | 64.74 | 4.88 | 11.96 | 9.12 | — |
| 14 | H | OMe | H | H | 5-OH | 70 | 2610.0 | 1660 | 2440.0 | | 870 (25.5) | 219-221 (d) | C₁₈H₁₅N₃O₂S·0.2H₂O | 64.82 63.40 63.14 | 4.77 4.55 4.47 | 11.86 12.32 12.26 | 9.15 9.40 9.23 | — |

(No. 2)

| Ex. No. | R¹ | R² | R³ | R⁴ | R | EtOH (ml) | KOH (mg) | Compd. (II-1) (mg) | Compd. (IV) (mg) | Compd. (Ia) No. | Yield (mg) (%) | (m.p.) (°C.) | Molecular Formula | Elemental Analysis (%) up: Calcd. down: Found C | H | N | S |
|---|---|---|---|---|---|---|---|---|---|---|---|---|---|---|---|---|---|
| 15 | H | OMe | OCH₂C≡CH | H | H | 18 | 268.2 | 408.6 | 226.8 | Ia-14 | 356.4 (68.6) | 196-198 | C₂₁H₁₇N₃O₂S·1/5H₂O | 66.54 66.50 | 4.63 4.56 | 11.09 10.86 | 8.46 8.26 |
| 16 | H | OMe | H | OMe | H | 120 | 3140.0 | 4400.0 | 2400.0 | Ia-15 | 1360.0 (24.3) | 187-189 | C₁₉H₁₇NSO₂·0.15H₂O | 64.40 64.20 | 4.92 4.99 | 11.87 11.58 | 9.05 8.77 |
| 17 | H | O—CH₂ — OMe △ | H | H | H | 10 | 270.0 | 430 | 210 | Ia-16 | 330.0 (61.1) | 203-205 | C₂₂H₂₁N₃SO₂ | 67.50 67.64 | 5.41 5.41 | 10.73 10.64 | 8.19 8.80 |
| 18 | H | O—i-pro | H | H | H | 20 | 410.0 | 570.0 | 320.0 | Ia-17 | 230.0 (30.7) | 164-166 | C₂₀H₁₉N₃SO·0.1AcOEt | 68.39 68.37 | 5.57 5.47 | 11.73 11.50 | 8.95 8.75 |

(No. 3)

| Ex. No. | R¹ | R² | R³ | R⁴ | R | Compd. (IV) (mg) | Compd. (Ia) No. | Yield (mg)/(%) | NMR |
|---|---|---|---|---|---|---|---|---|---|
| 19 | H | OMe | O—Al | H | H | 720 | Ia-18 | 650 (71.8) | (CDCl₃) 4.01(s, 3H); 4.56-4.72(m, 2H); 5.02(s, 2H); 5.70-6.30(m, 1H); 7.06-7.68(m, 7H); 8.35(d, J=6Hz, 1H) |
| 20 | H | OMe | O—Bz | H | H | 930 | Ia-19 | 810 (71.7) | (CDCl₃—d₆DMSO) 3.93(s, 3H); 5.00(s, 2H); 5.30(s, 2H); 7.00-7.76(m, 6H); 7.33(s, 5H); 7.87(s, 1H); 8.26(d, J=6Hz, 1H) |
| 21 | H | OCH₂C≡CH | H | H | H | 675.6 | Ia-20 | 569.1 (65.4) | (CDCl₃) 3.60(t, 1H); 4.98(d, 2H); 5.20(s, 2H); 7.05-7.75(m, 7H); 8.20-8.45(m, 2H); 12.60(b, 1H) |

EXAMPLE 22

1-Hydroxymethyl-2-[(6,7-dimethoxyisoquinolin-1-yl)methylthio]benzimidzole (Ib-1)

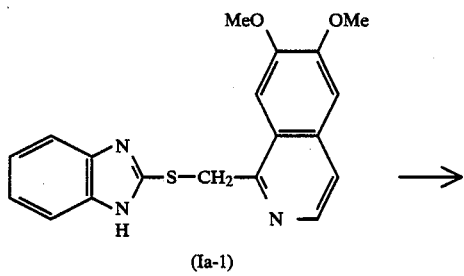

(Ia-1)

→

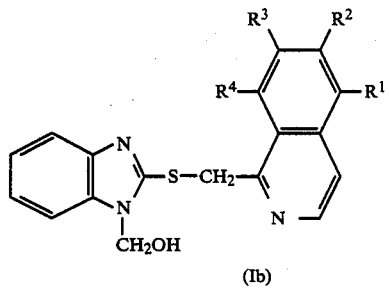

(Ib)

(wherein $R^1$, $R^2$, $R^3$ and $R^4$ have the same meaning as defined above).

In the same method as in Example 22, the reaction was performed under the reaction conditions as defined in Table 3, whereby the objective compounds (Ib) were obtained.

TABLE 3

| Ex. No. | $R^1$ | $R^2$ | $R^3$ | $R^4$ | Compd. (Ia) g | CH₃CN ml | HCHO ml | Compd. (Ib) Yield mg/(%) | No. | m.p. (°C.) | NMR or Elemental Analysis |
|---|---|---|---|---|---|---|---|---|---|---|---|
| 23 | H | OMe | H | H | 0.88 | 15.5 | 0.67 | 0.85 (88.5) | Ib-2 | — | (CDCl₃ - d₆DMSO) 3.69(s, 3H); 5.27(s, 2H); 5.65(s, 2H); 6.55(b, 1H); 7.16–8.46(m, 9H) |
| 24 | H | OMe | H | OMe | 0.7 | 11 | 0.49 | 0.65 (85.5) | Ib-3 | 163–165 | (for C₂₀H₁₉N₃SO₃) Calcd. (%): C, 62.98; H, 5.02; N, 11.02; S, 8.04 Found (%): C, 62.87; H, 4.86; N, 10.82; S, 8.14 |

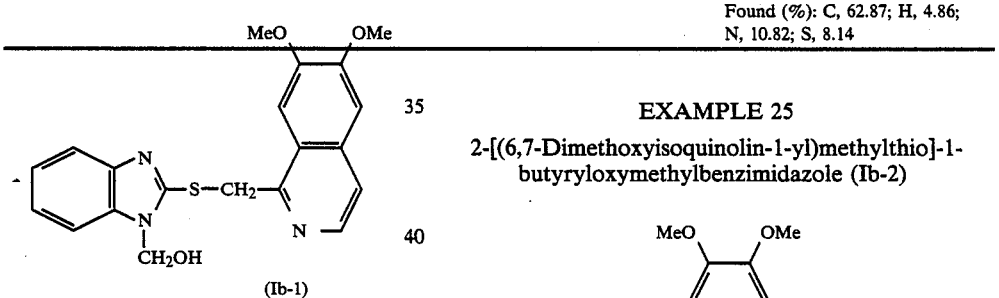

(Ib-1)

To a suspension of 702 mg of the compound (Ia-1) in 11 ml of CH₃CN was added 490 mg of 57% aqueous solution of HCHO, and the mixture was stirred for 30 min. at 70° C. It was filtered under cooling and washed with CH₃CN to give 705 mg of the objective compound 1-hydroxymethyl-2-[(6,7-dimethoxyisoquinolin-1-yl)methylthio]benzimidazole (Ib-1) (Yield: 92.8%).

m.p.: 156°–158° C. (d) (recrystallized from AcOEt)

Anal Calcd. (%) for C₂₀H₁₉N₃SO₃: C, 62.98; H, 5.02; N, 11.02; S, 8.40. Found (%): C, 63.03; H, 5.01; N, 10.86; S, 8.32.

EXAMPLE 23–24

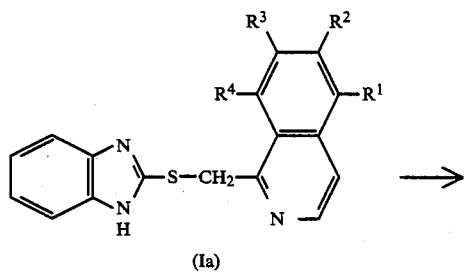

(Ia)

→

EXAMPLE 25

2-[(6,7-Dimethoxyisoquinolin-1-yl)methylthio]-1-butyryloxymethylbenzimidazole (Ib-2)

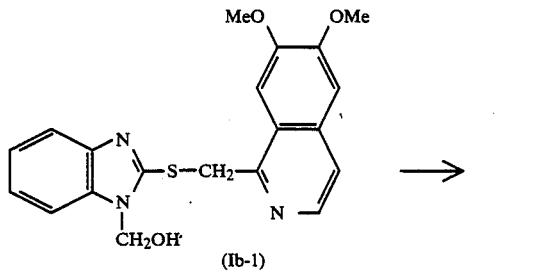

(Ib-1)

→

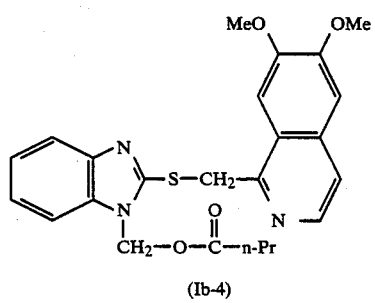

(Ib-4)

To a solution of 534 mg of the compound (Ib-1) in 12 ml of pyridine was added 0.67 ml of butyric anhydride, and the mixture was stirred for 4 hr. at room temperature. Under the reduced pressure, pyridine was evaporated, and the residue was extracted with CHCl₃, washed with water, dried and concentrated. The residue was subjected to silica gel column chromatography, eluting with AcOEt. Concentration of the eluate gave 540 mg of the objective compound 2-[(6,7-dimethoxyisoquinolin-1-yl)methylthio]-1-butyryloxymethyl-benzimidazole (Yield: 85.4%).

m.p.: 149°–151° C. (recrystallized from AcOEt).

Anal. Calcd. (%) for $C_{24}H_{25}N_3SO_4$: C, 63.84; H, 5.58; N, 9.31; S, 7.10. Found: (%): C, 63.89; H, 5.71; N, 9.24; S, 7.03.

EXAMPLE 26–28

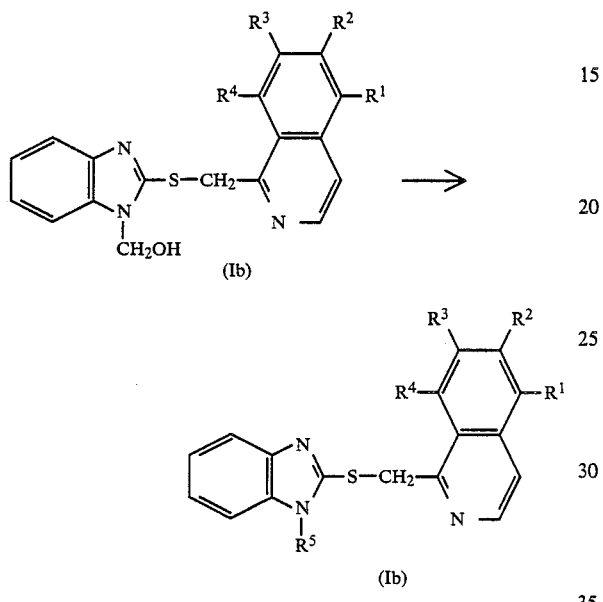

(wherein $R^1$, $R^2$, $R^3$ and $R^4$ have the same meanings as defined above).

In the same method as in Example 25, the reaction was performed under the reaction conditions as defined in Table 4, whereby the objective compounds (Ib) were obtained.

EXAMPLE 29

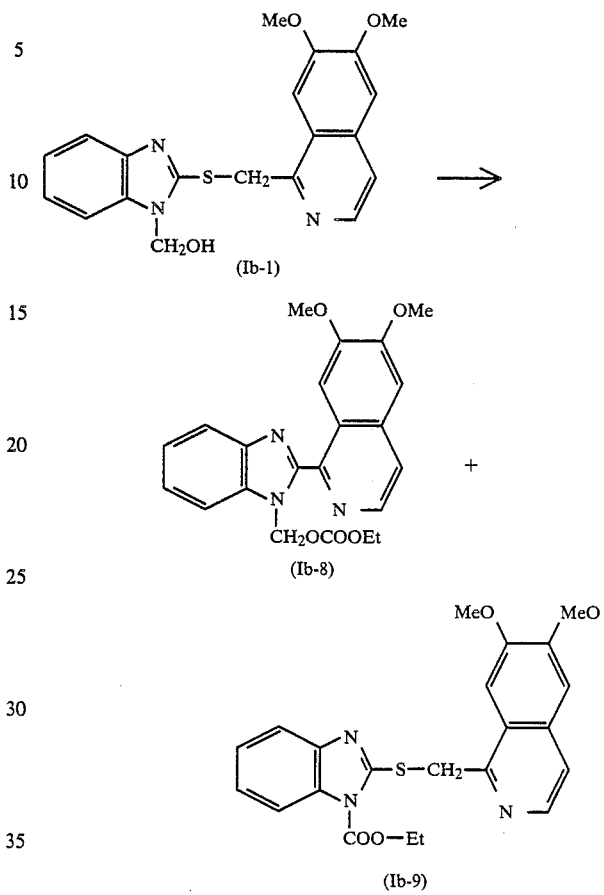

To a solution of 1.9 g of the compound (Ib-1) and 1.39 ml of $Et_3N$ in 120 ml of $CHCl_3$ was added 0.52 ml of ethyl chloroformate and the mixture was stirred for 2.5 hr. It was neutralized with saturated aqueous solution of $NaHCO_3$ and the $CHCl_3$ layer was dried and concentrated. The residue was subjected to silica gel column chromatography, eluting with $CHCl_3$-AcOEt (4:1 v/v).

TABLE 4

| Ex. No. | $R^1$ | $R^2$ | $R^3$ | $R^4$ | $R^5$ | Compd. (Ib) (g) | No. | Acid Anhydride (ml) | | Compd. (Ia) Yield g/(%) | No. | m.p. (°C.) | Elemental Analysis |
|---|---|---|---|---|---|---|---|---|---|---|---|---|---|
| 26 | H | OMe | H | H | CH₂—O—CO—n-Pro | 0.77 | Ib-2 | Butyric | 1.02 | 0.64 (58.1) | Ib-5 | 95–100 | (for $C_{23}H_{23}N_3SO_3.0.2H_2O$) Calcd. (%): C, 64.98; H, 5.55; N, 9.88; S, 7.54 Found (%): C, 65.05; H, 5.42; N, 9.59; S, 7.28 |
| 27 | H | OMe | H | OMe | CH₂—O—CO—n-Pro | 0.572 | Ib-3 | Butyric | 0.74 | 0.52 (76.8) | Ib-6 | 113–115 | (for $C_{24}H_{25}N_3SO_4$) Calcd. (%): C, 63.84; H, 5.58; N, 9.31; S, 7.10 Found (%): C, 63.89; H, 5.53; N, 9.09; S, 6.85 |
| 28 | H | OMe | OMe | H | CH₂—O—CO—CH₃ | 0.275 | Ib-1 | Acetic | 1.09 | 0.305 (100) | Ib-7 | 183–185 | (for $C_{22}H_{21}N_3SO_4$) Calcd. (%): C, 62.40; H, 5.00; N, 9.92; S, 7.57 Found (%): C, 62.50; H, 5.02; N, 9.87; S, 7.43 |

Concentration of the former fraction gave 840 mg of the objective compound 1-ethoxycarbonyl-2-[(6,7-dimethoxyisoquinolin-1-yl)methylthio]benzimidazole (Ib-9) (Yield: 40.0%).

m.p.: 194°–196° C. (recrystallized from AcOEt).

Anal. Calcd. (%) for $C_{22}H_{21}N_3SO_4$: C, 62.40; H, 5.00; N, 9.92; S, 7.57. Found (%): C, 62.37; H, 4.95; N, 9.80; S, 7.46.

Concentration of the latter fraction gave 1240 mg of the objective compound 1-ethoxycarbonyloxymethyl-2-[(6,7-dimethoxyisoquinolin-1-yl)methylthio]benzimidazole (Ib-8) (Yield: 54.9%).

m.p.: 161°–162° C. (recrystallized from AcOEt).

Anal Calcd. (%) for $C_{23}H_{23}N_3SO_5$: C, 60.91; H, 5.11; N, 9.27; S, 7.07. Found (%): C, 60.89; H, 5.19; N, 9.17; S, 7.21.

EXAMPLE 30

2-[(6,7-Dimethoxyisoquinolin-1-yl)methylsulfinyl]benzimidazole (Ic-1)

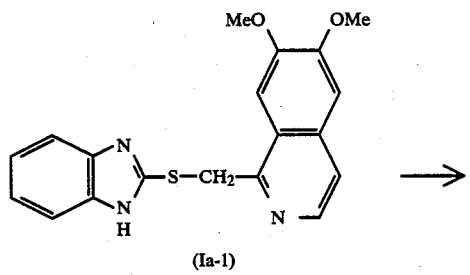

(Ia-1)

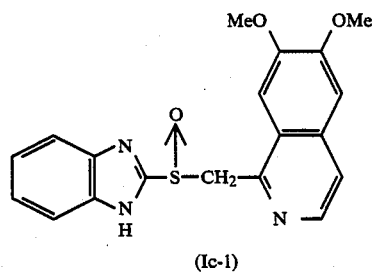

(Ic-1)

To a solution of 246.0 mg of 2-[(6,7-dimethoxyisoquinolin-1-yl)methylthio]benzimidazole (Ia-1) (0.700 mmol) in 10 ml of CHCl$_3$ was added 151.0 mg of 80% 3-CPBA (0.700 mmol) at −10°−−15° C., and the mixture was stirred for 30 min. at the same temperature. The reaction mixture was mixed with 3 ml of saturated aqueous solution of NaHCO$_3$ and 0.3 ml of 10% aqueous solution of NaHSO$_3$. The reaction temperature was returned to room temperature, and the reaction mixture was mixed with 2 ml of water and extracted with CHCl$_3$. The CHCl$_3$ layer was dried over anhydrous sodium sulfate and concentrated in vacuo. The residue was subjected to silica gel chromatography, eluting with AcOEt-MeOH. The obtained crystals were washed with CH$_2$Cl$_2$-benzene to give 216.2 mg of the objective compound 2-[(6,7-dimethoxyisoquinolin-1-yl)methylsulfinyl]benzimidazole (Ic-1) (Yield: 83.7%).

m.p.: 275°–278° C. (d).

Anal. Calcd. (%) for $C_{19}H_{17}N_3O_3S.1/10H_2O$: C, 61.80; H, 4.70; N, 11.38; S, 8.68. Found (%): C, 61.68; H, 4.70; N, 11.24; S, 8.71.

EXAMPLE 31–55

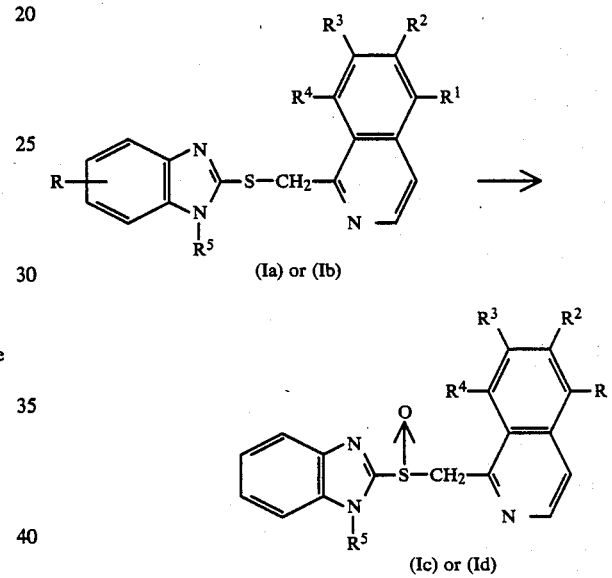

(wherein $R^1$, $R^2$, $R^3$, $R^4$, $R^5$ and R have the same meaning as defined above).

In the same method as in Example 30, the reaction was performed under the reaction conditions as defined in Table 5, whereby the objective compounds (Ic) and (Id) were obtained, respectively.

TABLE 5

| Ex. No. | R¹ | R² | R³ | R⁴ | R⁵ | R | Compd. (Ia) or (Ib) No. | Compd. (Ia) or (Ib) (mg) | m-CPBA (mg) | Compd. (Ic) or (Id) No. | m.p. (°C) (d) | Yield (mg) (%) | Molecular Formula | Elemental Analysis (%) up: Calcd. down: Found C | H | N | S | F |
|---|---|---|---|---|---|---|---|---|---|---|---|---|---|---|---|---|---|---|
| | | | | | | | (No. 1) | | | | | | | | | | | |
| 31 | H | H | OMe | H | H | H | Ia-2 | 286.0 | 192.0 | Ic-2 | 90–130* | 284.6 (91.1) | $C_{18}H_{15}N_3O_2S\cdot\frac{1}{4}H_2O$ | 61.61 61.69 | 4.74 4.88 | 11.97 11.75 | 9.14 8.85 | 13.59 13.36 |
| 32 | H | OMe | OMe | H | H | 5-CF₃ | Ia-3 | 255.3 | 129.4 | Ic-3 | 267–269 | 179.5 (67.8) | $C_{20}H_{16}N_3O_2SF_3\cdot\frac{1}{2}H_2O$ | 54.42 54.21 | 3.81 3.75 | 9.52 9.47 | 7.26 7.53 | 22.82 22.16 |
| 33 | H | OMe | OMe | H | H | 5-OMe | Ia-4 | 249.1 | 140.2 | Ic-4 | 255–260 | 244.5 (93.6) | $C_{20}H_{19}N_3O_4S\cdot\frac{1}{4}H_2O$ | 59.76 59.73 | 4.89 4.94 | 10.45 10.39 | 7.89 7.72 | — |
| 34 | OMe | OMe | OMe | H | H | H | Ia-5 | 288.8 | 161.8 | Ic-5 | 144–145 | 154.8 (51.7) | $C_{20}H_{19}N_3O_4S\cdot1/10H_2O$ | 60.17 60.18 | 4.85 4.81 | 10.52 10.50 | 8.03 8.00 | — |
| 35 | H | —OCH₂O— | | H | H | H | Ia-6 | 201.2 | 129.4 | Ic-6 | 150–153 | 172.6 (79.8) | $C_{18}H_{13}N_3O_3S\cdot\frac{1}{4}H_2O$ | 59.99 60.08 | 3.92 3.93 | 11.66 11.60 | 8.90 8.72 | — |
| 36 | H | OMe | OCH₂CF₃ | H | H | H | Ia-7 | 209.7 | 107.9 | Ic-7 | 185– | 179.5 (82.5) | $C_{20}H_{16}N_3O_3SF_3$ | 55.17 55.41 | 3.70 3.69 | 9.65 9.53 | 7.36 7.47 | 13.09 12.91 |
| 37 | H | OCH₂CF₃ | OMe | H | H | H | Ia-8 | 209.7 | 107.9 | Ic-8 | 180– | 183.6 (82.6) | $C_{20}H_{16}N_3O_3SF_3\cdot\frac{1}{2}H_2O$ | 54.05 54.20 | 3.86 3.96 | 9.45 9.18 | 7.21 7.49 | 12.82 12.44 |
| 38 | H | OCH₂CF₃ | OCH₂CF₃ | H | H | H | Ia-9 | 155.4 | 67.1 | Ic-9 | 187– | 110.2 (70.4) | $C_{21}H_{16}N_3O_3SF_6$ | 50.10 50.64 | 3.00 3.09 | 8.35 8.34 | 6.37 6.76 | 22.64 21.66 |
| 39 | H | O—Al | OMe | H | H | H | Ia-10 | 630.0 | 380.0 | Ic-10 | 155–160 | 520.0 (78.7) | $C_{21}H_{19}N_3SO_3$ | 64.11 63.90 | 4.87 5.04 | 10.68 10.51 | 8.15 7.91 | — |
| | | | | | | | (No. 2) | | | | | | | | | | | |
| 40 | H | OMe | OCH₂C≡CH | H | H | H | Ia-3 | 303.2 | 172.0 | Ic-11 | 142–145 | 233.1 (13.6) | $C_{21}H_{17}N_3O_3S\cdot\frac{1}{4}H_2O$ | 63.70 63.67 | 4.45 4.22 | 10.61 10.68 | 8.10 7.81 | — |
| 41 | H | OCH₂C≡CH | H | H | H | H | Ia-20 | 174.4 | 108.9 | Ic-12 | 160–161 | 165.5 (89.6) | $C_{20}H_{16}N_3O_2S\cdot\frac{1}{4}H_2O$ | 65.65 65.57 | 4.27 4.42 | 11.48 11.25 | 8.76 8.50 | — |
| 42 | H | OMe | O—Al | H | H | H | Ia-18 | 630.0 | 360.0 | Ic-13 | 156–158 | 530.0 (80.3) | $C_{21}H_{19}N_3O_3S$ | 64.11 63.80 | 4.87 4.97 | 10.68 10.60 | 8.15 7.89 | — |
| 43 | H | OMe | O—Bz | H | H | H | Ia-19 | 780.0 | 400.0 | Ic-14 | 161–163 | 610.0 (80.9) | $C_{25}H_{21}N_3O_3S$ | 67.70 67.45 | 4.77 4.69 | 9.47 9.19 | 7.23 7.02 | — |
| 44 | H | O—Al | H | H | H | H | Ia-11 | 150.0 | 100.0 | Ic-15 | 155–158 | 130.0 (82.8) | $C_{20}H_{17}N_3SO_2$ | 66.10 66.10 | 4.72 4.78 | 11.50 11.36 | 8.82 8.73 | — |
| 45 | H | OMe | H | H | H | H | Ia-12 | 2560.0 | 1800.0 | Ic-16 | 154–156 | 2200 (85.9) | $C_{18}H_{16}N_3SO_2$ | 64.08 64.06 | 4.48 4.32 | 12.45 12.17 | 9.50 9.28 | — |
| 46 | H | O—CH₂⟨△⟩ | OMe | H | H | H | Ia-16 | 285.0 | 165.0 | Ic-17 | 176–178 | 240.0 (80.8) | $C_{22}H_{21}N_3SO_3$ | 64.85 64.58 | 5.19 5.31 | 10.31 10.04 | 7.87 7.62 | — |
| 47 | H | O—i-Pro | H | H | H | H | Ia-17 | 190.0 | 120.0 | Ic-18 | 168–190 | 130.0 (65.3) | $C_{20}H_{19}N_3SO_2$ | 65.73 65.72 | 5.24 5.35 | 11.50 11.30 | 8.77 8.51 | — |
| | | | | | | | (No. 3) | | | | | | | | | | | |
| 48 | H | OMe | H | OMe | H | H | Ia-15 | 190.0 | 120.0 | Ic-19 | 158–160 | 150.0 (75.4) | $C_{19}H_{17}N_3SO_3$ | 62.11 62.17 | 4.66 4.60 | 11.44 11.26 | 8.73 8.66 | — |
| 49 | H | OMe | H | H | CH₂—O—CO—n-Pr | H | Ib-5 | 580.0 | 320.0 | Id-1 | 111–113 | 270.0 (45.0) | $C_{23}H_{23}N_3SO_4$ | 63.14 63.12 | 5.30 5.31 | 9.60 9.47 | 7.33 7.17 | — |
| 50 | H | OMe | H | OMe | CH₂—O—CO—n-Pr | H | Ib-6 | 410.0 | 200.0 | Id-2 | 125–127 | 170.0 (40.0) | $C_{24}H_{26}N_3SO_6$ | 61.66 61.62 | 5.39 5.39 | 8.99 8.85 | 6.68 6.86 | — |
| 51 | H | OMe | OMe | H | CH₂—O—CO—n-Pr | H | Ib-4 | 497.0 | 237.0 | Id-3 | 110–112 | 210.0 (40.8) | $C_{24}H_{26}N_3SO_6$ | 61.66 61.62 | 5.39 5.32 | 8.99 8.84 | 6.86 6.73 | — |

TABLE 5-continued

| | | | | | | | | | | | | | | C | H | N | |
|---|---|---|---|---|---|---|---|---|---|---|---|---|---|---|---|---|---|
| 52 | H | OMe | OMe | H | CH$_2$OCOOEt | H | 1130.0 | 540.0 | 540.0 (46.2) | Id-4 | 156–158 | C$_{23}$H$_{23}$N$_3$SO$_6$ | 58.84 58.59 | 4.94 5.00 | 8.95 8.81 | 6.83 6.76 | — — |
| 53 | H | OMe | OMe | H | COOEt | H | 760.0 | 390.0 | 240.0 (30.6) | Id-5 | 160–162 | C$_{22}$H$_{21}$N$_3$SO$_6$ | 60.13 60.13 | 4.82 4.64 | 9.56 9.40 | 7.29 7.14 | — — |
| 54 | H | OMe | H | 5-OH | H | H | 440.0 | 300.0 | 380.0 (82.1) | Ic-20 | 184–186 | C$_{18}$H$_{16}$N$_3$SO$_3$·0.25H$_2$O | 60.24 59.95 | 4.63 4.24 | 11.71 11.60 | 8.93 8.90 | — — |
| 55 | H | OMe | OMe | H | CH$_2$—O—CO—CH$_3$ | H | 254.0 | 130.0 | 105.0 (39.9) | Id-7 | 151–154 | C$_{22}$H$_{21}$N$_3$SO | 60.13 59.94 | 4.82 4.75 | 9.56 9.47 | 7.29 7.08 | — — |

EXAMPLE 56

2-[(7-Allyloxy-6-methoxyisoquinolin-1-yl)methylsulfinyl]-1-pivaloyloxymethylbenzimidazole (Id-7)

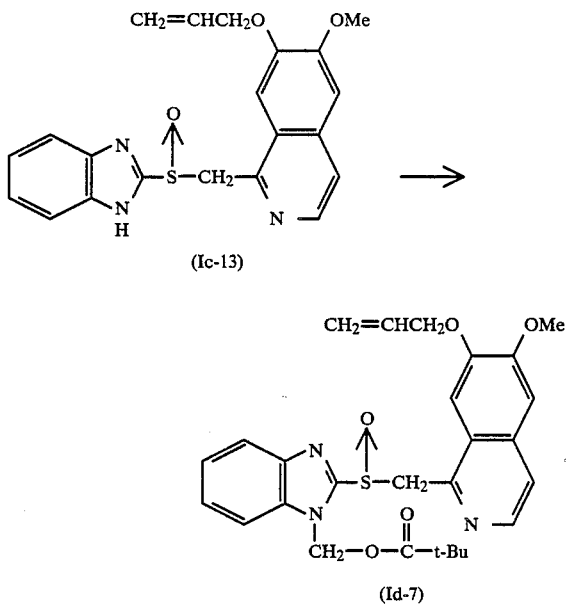

To a solution of 410 mg of the compound (Ic-13) in 20 ml of DMF was added 46 mg of 60% NaH (mineral oil suspension), and the mixture was stirred for 30 min., mixed with 0.158 ml of chloromethyl pivalate, stirred for 7 hr. and concentrated in vacuo. The residue was extracted with CHCl₄ and washed with water. The CHCl₃ layer was dried and concentrated. The residue was subjected with silica gel column chromatography, eluting with AcOEt. Concentration of the eluate gave 160 mg of the objective compound 2-[(7-allyloxy-6-methoxyisoquinolin-1-yl)methylsulfinyl]-1-pivaloyloxymethylbenzimidazole (Id-7) (Yield: 30.2%).

m.p.: 132°–134° C. (d).

Anal. Calcd. (%) for $C_{27}H_{29}N_3SO_5$: C, 63.89; H, 5.76; N, 8.28; S, 6.32. Found (%): C, 63.86; H, 5.87; N, 8.09; S, 6.24.

EXAMPLE 57

2-[(6-Methoxyisoquinolin-1-yl)methylsulfinyl]-1-pivaloyloxymethylbenzimidazole (Id-8)

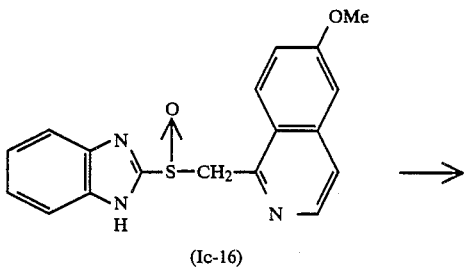

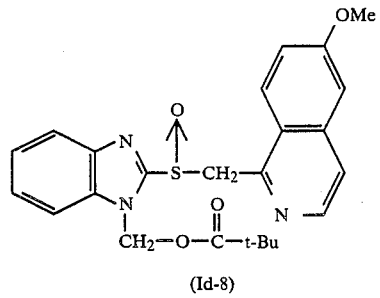

In the same method as in Example 56, 675 mg of the compound (Ic-16) was allowed to react with 88 mg of 60% NaH (mineral oil suspension) and 0.3 ml of chloromethyl pivalate in 10 ml of DMF to give 0.28 g of the objective compound 2-[(6-methoxyisoquinolin-1-yl)methylsulfinyl]-1-pivaloylmethylbenzimidazole (Id-8) (Yield: 31.3%).

m.p.: 125°–127° C. (d).

Anal. Calcd. (%) for $C_{24}H_{25}N_3SO_4$: C, 63.84; H, 5.58; N, 9.31; S, 7.10. Found (%): C, 63.78; H, 5.69; N, 9.04; S, 6.90.

EXAMPLE 58

2-[(6,7-Dimethoxyisoquinolin-1-yl)methylsulfinyl]-1-pivaloyloxymethylbenzimidazole (Id-9)

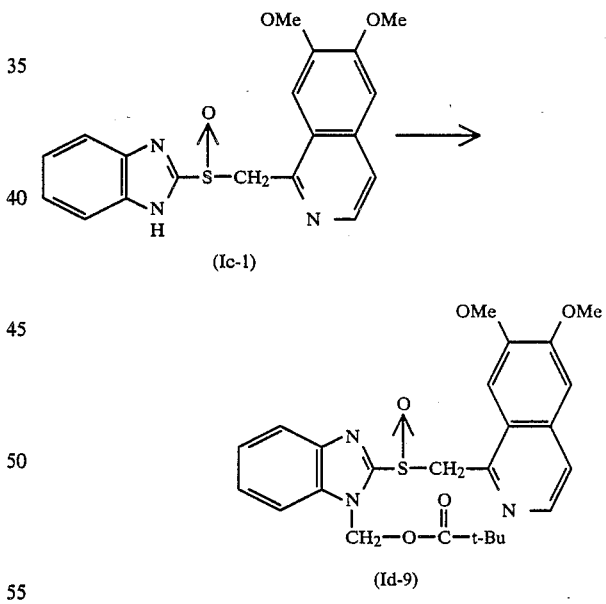

In the same method as in Example 56, 331 mg of the compound (Ic-1) was allowed to react with 40 mg of 60% NaH (mineral oil suspension) and 142 mg of chloromethyl pivalate in 10 ml of DMF to give 210 mg of the objective compound 2-[(6,7-dimethoxyisoquinolin-1-yl)methylsulfinyl]-1-pivaloyloxymethylbenzimidazole (Id-9) (Yield: 48.4%).

m.p.: 114°–116° C. (d).

Anal. Calcd. (%) for $C_{25}H_{27}N_3SO_5$: C, 62.35; H, 5.65; N, 8.73; S, 6.66. Found (%): C, 62.33; H, 5.87; N, 8.58; S, 6.50.

EXAMPLE 59

2-[(7-Benzyloxy-6-methoxy)isoquinolin-1-yl]methylsulfinyl}-1-pivaloyloxymethylbenzimidazole (Id-10)

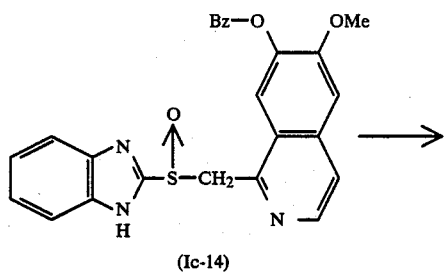

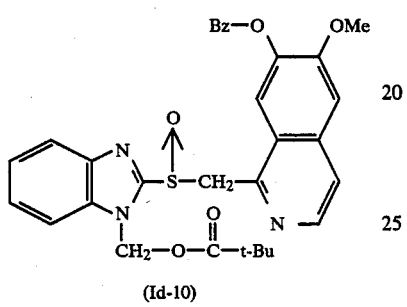

In the same method as in Example 56, 490 mg of the compound (Ib-11) was allowed to react with 49 mg of 60% NaH (mineral oil suspension) and 167 mg of chloromethyl pivalate in 20 ml of DMF to give 240 mg of the objective compound 2-[(7-benzyloxy-6-methoxy)isoquinolin-1-yl]methylsulfinyl}-1-pivaloyloxymethylbenzimidazole (Id-10) (Yield: 37.5%).

m.p.: 161°–162° C. (d).

Anal Calcd. (%) for $C_{31}H_{31}N_3O_5$: C, 66.77; H, 5.60; N, 7.54; S, 5.75. Found (%): C, 66.72; H, 5.66; N, 7.50; S, 5.60.

EXAMPLE 60

2-(6,7-Dimethoxyisoquinolin-1-yl)methylsulfinyl-1-phthalidylbenzimidazole (Id-11)

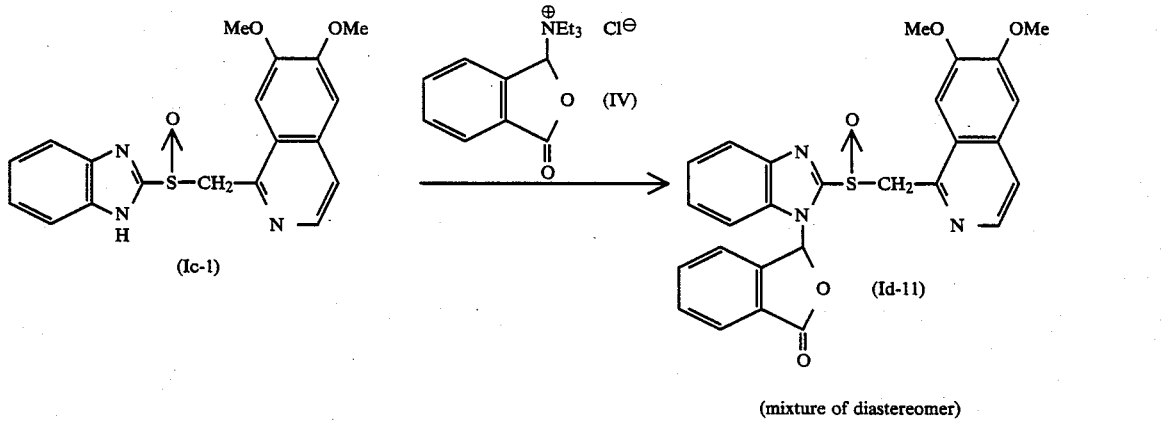

(mixture of diastereomer)

To 102.0 mg of 3-chlorophthalide (0.605 mmol) were added 1.1 ml of dry DMF and 83.5 mg of Et$_3$N (0.825 mmol), and the mixture was heated for 1.5 hr. at 65°–70° C. to give the compound (VI). To the compound (VI) were added 91.2 mg of K$_2$CO$_3$ (0.66 mmol), 205.4 mg of 2-[(6,7-dimethoxyisoquinolin-1-yl)methylsulfinyl]benzimidazole.½H$_2$O (0.55 mmol) and 1.3 ml of dry DMF, and the mixture was stirred for 2.5 hr. at room temperature, washed with water and extracted with CHCl$_3$. The CHCl$_3$ layer was dried over anhydrous sodium sulfate and concentrated in vacuo. The residue was subjected to silica gel column chromatography, eluting with AcOEt. The obtained crystals were washed with AcOEt to give 248.0 mg of the objective compound 2-(6,7-dimethoxyisoquinolin-1-yl)methylsulfinyl-1-phthalydilbenzimidazole (Id-10) (mixture of diastereomer: Yield: 88.7%).

m.p.: 183.0°–184.4° C. (d).

Anal Calcd. (%) for $C_{27}H_{21}N_3O_5S.½H_2O$: C, 63.77; H, 4.36; N, 8.26; S, 6.30. Found (%): C, 63.96; H, 4.24; N, 8.13; S, 6.10.

EXAMPLE 61

2-{[6-Methoxy-7-(2,2,2-trifluoroethoxy)isoquinolin-1-yl]methylthio}-1-pivaloyloxymethylbenzimidazole (Ib-10)

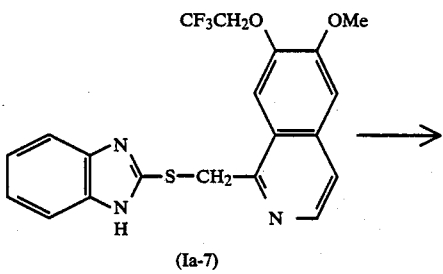

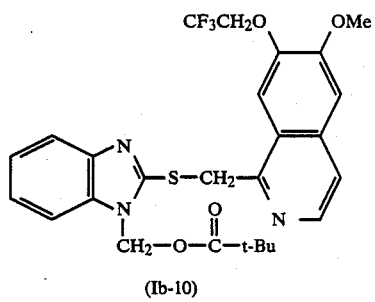

To a solution of 30.8 mg of 60% NaH (0.77 mmol) in 5 ml of dry DMF was added 293.6 mg of 2-{[6-methoxy-7-(2,2,2-trifluoroethoxy)isoquinolin-1-yl]methylthio}benzimidazole (Ia-7) (0.7 mmol) and the mixture was stirred for 10 min. at room temperature. The mixture was mixed with 126.5 mg of chloromethyl pivalate, stirred for 2 hr. at room temperature and allowed to stand overnight. After DMF was distilled off in vacuo, the residue was mixed with water and extracted with CH$_2$Cl$_2$. The CH$_2$Cl$_2$ layer was dried over anhydrous sodium sulfat4e and concentrated. The residue was subjected to silica gel column chromatography, eluting with CH$_2$Cl$_2$-AcOEt. Crude product was washed with cyclohexane to give 344.7 mg of the objective compound 2-{[6-methoxy-7-(2,2,2-trifluoroethoxy)isoquinolin-1-yl]methylthio}-1-pivaloyloxymethyl-benzimidazole (Ib-10) (Yield: 92.3%).

m.p.: 160.5°–162.0° C.

Anal Calcd. (%) for C$_{26}$H$_{26}$N$_3$O$_4$SF$_3$: C, 58.53; H, 4.91; N, 7.88; S, 6.01; F, 10.68. Found (%): C, 58.38; H, 4.86; N, 7.77; S, 6.18; F, 10.90.

EXAMPLE 62

2-{[6-Methoxy-7-(2,2,2-trifluoroethoxy)isoquinolin-1-yl]methylsulfinyl}-1-pivaloyloxymethylbenzimidazole (Id-12)

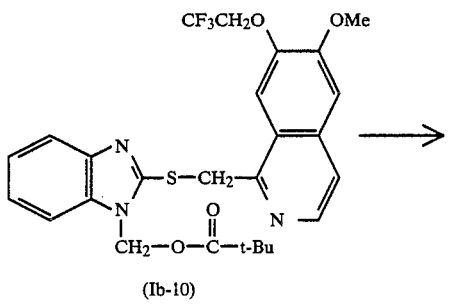

(Ib-10)

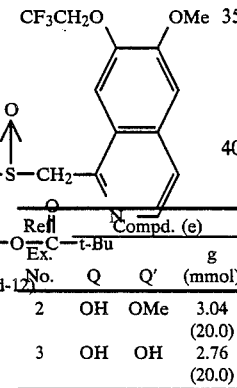

(Id-12)

In the same method as in Example 30, 324.0 mg of the compound (Ib-10) was allowed to react with 261.9 mg of 80% m-CPBA in 30 ml of CHCl$_3$ to give 135.4 mg of the objective compound 2-{[6-Methoxy-7-(2,2,2-trifluoroethoxy)isoquinolin-1-yl]methylsulfinyl}-1-pivaloyloxymethylbenzimidazole (Id-12) (Yield: 40.6%).

m.p.: 139.0°–140.5° C. (d).

Anal Calcd. (%) for C$_{26}$H$_{26}$N$_3$O$_5$SF$_3$: C, 56.82; H, 4.77; N, 7.65; S, 5.83; F, 10.37. Found (%): C, 57.00; H, 4.84; N, 7.48; S, 6.08; F, 10.25.

REFERENCE EXAMPLE 1

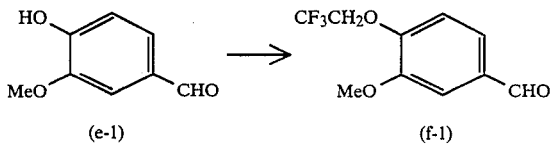

To a solution of 3.96 g of vaniline (e-1) (26.0 mmol) in 26 ml of dry DMF was added 1.04 g of 60% NaH (26.0 mmol) slowly, and the mixture was stirred for 30 min. in a stream of nitrogen. 2,2,2-Trifluoroethyl trifluoromethanesulfonate (6.64 g: 28.6 mmol) was added dropwise to the mixture and stirred overnight at room temperature. The reaction solution was poured into water and extracted with ether. The ether layer was washed with water, dried over anhydrous sodium sulfate and concentrated under reduced pressure. The residue was subjected to silica gel column chromatography, eluting with benzene-AcOEt to give 5.98 g of the objective compound 3-methoxy-4-(2,2,2-trifluoroethoxy)benzaldehyde (f-1) (Yield: 98.2%).

IR $\lambda_{max}^{CHCl_3}$: 1260, 1690, 1595 (cm$^{-1}$).

REFERENCE EXAMPLE 2-3

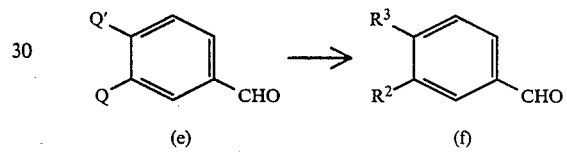

(wherein R$^2$ and R$^3$ each has the same meaning as defined above, and Q and Q' each is hydroxy or methoxy).

In the same manner as in Reference Example 1, the reaction was performed under the reaction conditions as defined in Table 6, whereby the objective compounds (f) was obtained.

TABLE 6

| Ref. Ex. No. | Compd. (e) | | | DMF (ml) | Compd. (f) | | | | IR (CHCl$_3$) cm$^{-1}$ |
|---|---|---|---|---|---|---|---|---|---|
| | Q | Q' | g (mmol) | | R$^2$ | R$^3$ | Yield g (%) | No. | |
| 2 | OH | OMe | 3.04 (20.0) | 20 | OCH$_2$CF$_3$ | OMe | 4.65 (99.3) | f-2 | 1260, 1165, 1690 |
| 3 | OH | OH | 2.76 (20.0) | 30 | OCH$_2$CF$_3$ | OCH$_2$CF$_3$ | 5.62 (93.0) | f-3 | 1160, 1250, 1690 |

REFERENCE EXAMPLE 4

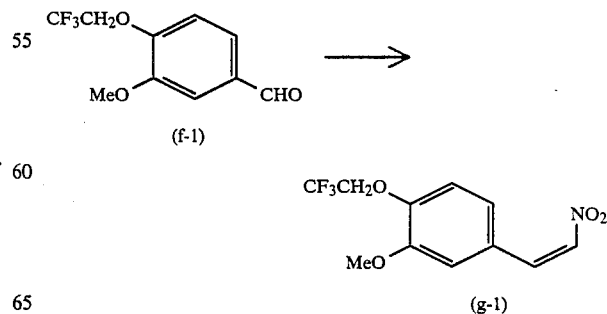

To a mixture of 2.81 g of the compound (f-1) (12.0 mmol), 20 ml of EtOH and 1.46 g of nitromethane (24.0 mmol) were added dropwise 1.96 g of 86% of KOH (30.0 mmol), 3 ml of water and 45 ml of MeOH under ice cooling, and the mixture was stirred for 30 min. at the same temperature. The reaction solution was poured into 30 ml of 15% HCl. The precipitated crystals were collected by filtration, washed with water and dried to give 2.90 g of the crude crystals. It is subjected to silica gel column chromatography, eluting with benzene-AcOEt to give 2.31 g of the objective compound 1-(2-nitroethenyl)-3-methoxy-4-(2,2,2-trifluoroethoxy)-benzene (g-1) (Yield: 69.4%).

IR $\nu_{max}^{CHCl_3}$: 1260, 1160, 1335 (cm$^{-1}$).

REFERENCE EXAMPLE 5-6

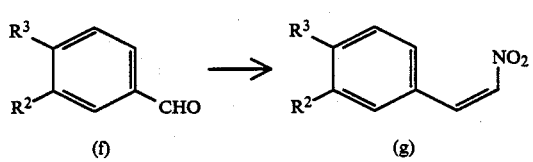

(f)

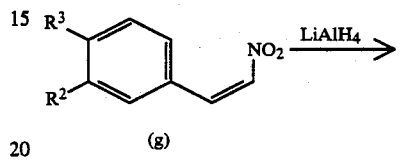

(g)

(wherein $R^2$ and $R^3$ have the same meaning as defined above).

In the same manner as in Reference Example 4, the reaction was performed under the reaction conditions as defined in Table 7, whereby the objective compounds (g) were obtained.

stirring for 2 hr., the mixture was mixed with 1.2 ml of AcOEt, 10 ml of hydrous ether and 6 ml of water in order under ice cooling. The temperature of the mixture was returned to room temperature and it was stirred for 1 hr. The mixture was filtered with a filtration aid and washed with THF. The crude objective compound 1-(2-aminoethyl)-3-methoxy-4-(2,2,2-trifluoroethoxy)-benzene (h-1) (1.97 g; Yield: 95.0%) was obtained by concentrating in vacuo.

NMR $\delta^{CDCl_3}$: 1.42 (s, 2H); 2.57–3.05 (m, 4H); 3.85 (s, 3H); 4.34 (q, 2H); 6.60–7.00 (3H).

REFERENCE EXAMPLE 8-9

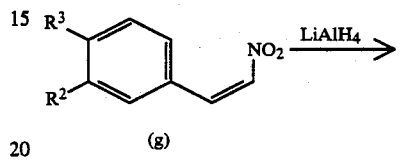

(g)

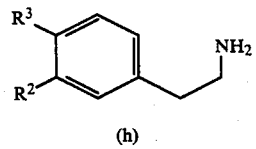

(h)

(wherein $R^2$ and $R^3$ each has the same meaning as defined above).

TABLE 7

| Ref. Ex. No. | R² | R³ | Compd. (f) (g) (mmol) | No. | EtOH (ml) | CH₃NO₂ (g) | KOH (g) | H₂O (ml) | MeOH (ml) | HCl (ml) | Compd. (g) Yield (g)/(%) | No. | I R (cm⁻¹) |
|---|---|---|---|---|---|---|---|---|---|---|---|---|---|
| 5 | OCH₂CF₃ | OMe | 4.63 (19.8) | f-2 | 36 | 2.42 | 3.23 | 5.0 | 7.3 | 50 | 3.75 (68.3) | g-2 | (Nujol) 1260, 1180, 1330 |
| 6 | OCH₂CF₃ | OCH₂CF₃ | 3.02 (10.0) | f-3 | 17 | 1.22 | 1.63 | 2.5 | 3.1 | 25 | 1.63 (47.2) | g-3 | (CHCl₃) 1160, 1250, 1280 |

REFERENCE EXAMPLE 7

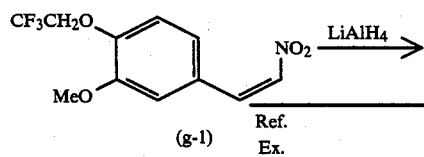

(g-1)

In the same method as in Reference Example 7, the reaction was performed under the reaction conditions as defined in Table 8, whereby the objective compounds (h) were obtained.

TABLE 8

| Ref. Ex. No. | R² | R³ | Compd. (g) (g) (mmol) | No. | THF (ml) | LiAlH₄ (g) (mmol) | Compd. (h) Yield (g)/(%) | No. | NMR δ (CDCl₃) |
|---|---|---|---|---|---|---|---|---|---|
| 8 | OCH₂CF₃ | OMe | 3.74 (13.5) | g-2 | 75 | 2.56 (67.5) | 3.23 (99.2) | h-2 | 1.43(s, 2H); 2.55–3.03(m, 4H); 3.83(s, 3H); 4.36(q, 2H); 6.70–7.05(3H) |
| 9 | OCH₂CF₃ | OCH₂CF₃ | 1.61 (4.66) | g-3 | 29 | 1.22 (23.3) | 1.44 (97.4) | h-3 | 1.43(s, 2H); 2.55–3.05(m, 4H); 4.34, 4.36(q,q, 2H, 2H); 6.75–7.10(3H) |

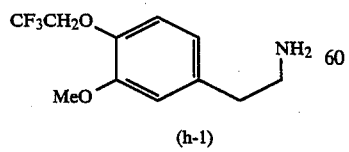

(h-1)

Under a nitrogen current 1.58 g of LiAlH₄ (41.6 mmol) was added to 15 ml of dry THF, and the mixture was dropwise added with 2.31 g of the compound (g-1) (8.32 mmol) and 30 ml of dry THF at 20°–25° C. After

REFERENCE EXAMPLE 10

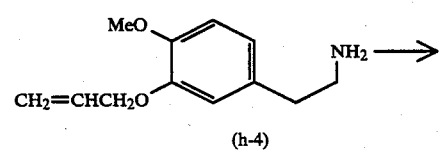

(h-4)

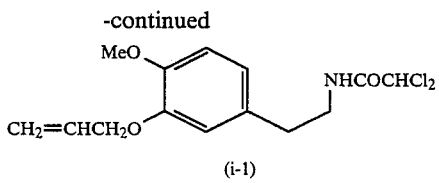

(i-1)

A solution of 3.05 g of 3-allyloxy-4-methoxyphenethylamine (h-4) and 2.52 g of dichloromethyl acetate was stirred at 100° C. for 45 min. The mixture was concentrated under reduced pressure. The residue was subjected to silica gel column chromatography, eluting with $CHCl_3$. Concentration of the eluate gave 2.18 g of the objective compound N-(3-allyloxy-4-methoxyphenethy)dichloroacetamide (i-1) (Yield: 68.8%).

m.p.: 88°–90° C. (recrystallized from AcOEt).

Anal Calcd. (%) for $C_{14}H_{17}Cl_2O_3$: C, 52.85; H, 5.39; N, 4.40; Cl, 22.28. Found (%): C, 52.64; H, 5.42; N, 4.39; Cl, 22.00.

REFERENCE EXAMPLES 11–22

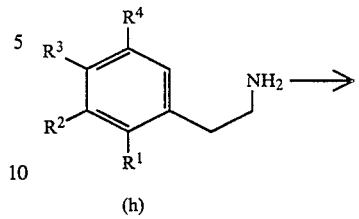

(h)

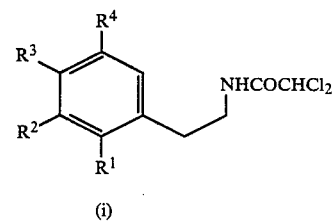

(i)

(wherein $R^1$, $R^2$, $R^3$ and $R^4$ each have the same meaning as defined above).

In the same method as in Reference Example 10, the reaction was performed under the reaction conditions as defined in Table 9, whereby the objective compounds (i) were obtained.

TABLE 9

(No. 1)

| Ref. Ex. No. | $R^1$ | $R^2$ | $R^3$ | $R^4$ | Compd. (h) g | $CH_3OCOCHCl_2$ (g) | Reaction Time (hr) | Yield (g) (%) | No. | NMR($CDCl_3$) or IR$\nu$($CHCl_3$)cm$^{-1}$ |
|---|---|---|---|---|---|---|---|---|---|---|
| 11 | H | OMe | O—Al | H | 1.6 | 1.32 | 1.0 | 1.3 (52.8) | i-2 | NMRδ($CDCl_3$): 2.82(T, J=7Hz, 2H)3.59(q, J=7Hz, 2H); 3.87(s, 3H) 4.53–4.70(m, 2H)5.20–5.57(m, 2H) 5.90(s, 1H); 5.90–6.36(m, 1H) 6.55(bs, 1H); 6.63–6.97(m, 3H) |
| 12 | H | O—Al | H | H | 1.4 | 1.36 | 1.0 | 0.88 (38.6) | i-3 | NMRδ($CDCl_3$): 2.85(t, J=7Hz, 2H)3.60(q, J=7Hz, 2H); 4.47–5.20(m, 2H)5.20–5.62(m, 2H); 5.90(-m, 2H)-5.90--6.4-0(m, 1H); 6.65(bs, 1H)6.73–6.99(m, 2H); 7.10–7.40(m, 1H) |
| 13 | H | OMe | $OCH_2CF_3$ | H | 1.96 | 1.35 | 0.25 | 1.91 (67.5) | i-4 | IR$\nu$($CHCl_3$): 1690, 1155, 1260 |
| 14 | H | $OCH_2CF_3$ | OMe | H | 3.22 | 2.22 | 0.25 | 2.81 (60.5) | i-5 | IR$\nu$($CHCl_3$): 1690, 1155, 1255 |
| 15 | H | $OCH_2CF_3$ | $OCH_2CF_3$ | H | 1.43 | 0.77 | 0.25 | 1.27 (65.8) | i-6 | IR$\nu$($CHCl_3$): 1160, 1255, 1290 |
| 16 | H | OMe | $OCH_2C{\equiv}CH$ | H | 1.09 | 0.91 | 0.25 | 0.72 (42.7) | i-7 | IR$\nu$($CHCl_3$): 1690, 1505, 1260 |
| 17 | H | O—$CH_2$—cyclopropyl | $OCH_3$ | H | 2.2 | 1.70 | 1.0 | 1.64 (49.7) | i-8 | NMRδ($CDCl_3$): 0.23–0.76(m, 4H) 1.10–1.53(m, 1H); 2.78(t, JH, 2H)3.55(q, J=7Hz, 2H); 3.85(s, 3H) 5.88(s, 1H); 6.55(bs, 1H) 6.13–6.86(m, 3H) |
| 18 | H | $OCH_2C{\equiv}CH$ | H | H | 2.03 | 1.99 | 1.0 | 1.90 (57.3) | i-9 | IR$\nu$($CHCl_3$): 1685, 1520, 1580 |

(No. 2)

| Ref. Ex. No. | $R^1$ | $R^2$ | $R^3$ | $R^4$ | Compd. (i) g | $CH_3OCOCHCl_2$ (g) | Reaction Time (hr) | Yield (g) (%) | No. | Molecular Formula | Elemental Analysis (%) Up: Calcd. Down: Found | | | |
|---|---|---|---|---|---|---|---|---|---|---|---|---|---|---|
| | | | | | | | | | | | C | H | N | Cl |
| 19 | H | OMe | O—Bz | H | 1.18 | 0.77 | 1.5 | 0.97 (63.0) | i-9 | $C_{18}H_{19}NCl_2O_3$ | 58.71 57.93 | 5.20 5.06 | 3.80 3.75 | 19.25 19.52 |

TABLE 9-continued

| 20 | H | OMe | H | H | 2.92 | 3.3 | 1.0 | 2.30 (45.5) | i-10 | $C_{11}H_{13}NCl_2O_2$ | 50.40 | 5.00 | 5.34 | 27.05 |
|----|---|-----|---|---|------|-----|-----|-------------|------|------------------------|-------|------|------|-------|
|    |   |     |   |   |      |     |     |             |      |                        | 50.40 | 4.97 | 5.46 | 26.78 |
| 21 | H | O—i-Pro | H | H | 3.62 | 3.46 | 1.0 | 3.30 (56.3) | i-11 | $C_{13}H_{17}NCl_2O_2$ | 53.81 | 5.91 | 4.83 | 24.23 |
|    |   |     |   |   |      |     |     |             |      |                        | 53.57 | 5.78 | 4.98 | 24.56 |
| 22 | H | OMe | H | OMe | 3.60 | 3.40 | 1.0 | 2.66 (45.9) | i-12 | $C_{12}H_{16}NCl_2O_3$ | 49.33 | 5.18 | 4.79 | 24.43 |
|    |   |     |   |   |      |     |     |             |      |                        | 49.20 | 5.13 | 4.76 | 24.44 |

REFERENCE EXAMPLE 23

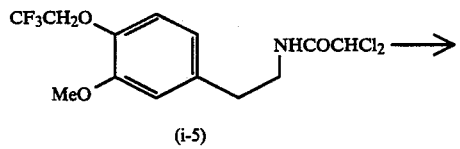

(i-5)

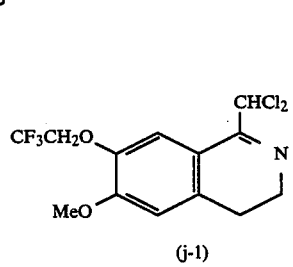

(j-1)

To 1.18 g of N-[3-methoxy-4-(2,2,2-trifluoroethoxy)-phenyl]dichloroacetamide (3.28 mmol) were added 8 ml of xylene and 4.02 g of $POCl_3$ (26.2 mmol), and the mixture was refluxed for 2 hr. Xylene was distilled off under reduced pressure and ether was added to the residue. Then the mixture was extracted with 10% HCl. The HCl layer was basified with 30% NaOH and extracted with ether. The ether layer was dried over anhydrous sodium sulfate and concentrated in vacuo to give viscous liquid. It was subjected to silica gel column chromatography, eluting with $CH_2Cl_2$-AcOEt to give 560.1 mg of the objective compound 1-dichloromethyl-6-methoxy-7-(2,2,2-trifluoroethoxy)-3,4-dihydroisoquinoline (j-1) (Yield: 49.9%) as crystals.

IR $\nu_{max}^{CHCl_3}$: 1155, 1270, 1320 (cm$^{-1}$).

REFERENCE EXAMPLE 24–34

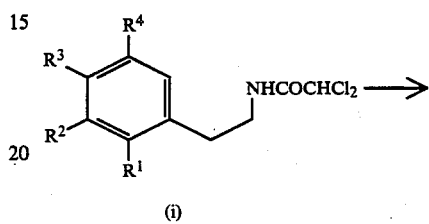

(i)

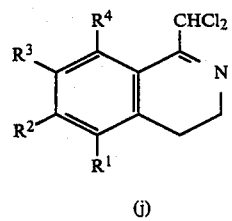

(j)

(wherein $R^2$ and $R^3$ have the same meaning as defined above).

In the same method as in Reference Example 23, the reaction was performed under the reaction conditions as shown in Table 10, whereby the objective compounds (j) were obtained.

TABLE 10

(No. 1)

| Ref. Ex. No. | $R^1$ | $R^2$ | $R^3$ | $R^4$ | Compd. (i) g | xylene (ml) | $POCl_3$ (ml) | Reaction Time (hr) | Compd. (j) Yield (g) (%) | No. | NMR (CDCl$_3$) |
|---|---|---|---|---|---|---|---|---|---|---|---|
| 24 | H | O—Al | OMe | H | 1.85 | 15 | 4.23 | 2 | 1.02 (58.5) | j-2 | 2.5–2.80(m, 2H); 3.63–3.96(m, 2H) 3.91(s, 3H); 4.57–4.83(m, 2H) 5.20–5.60(m, 2H); 6.73–6.33(m, 1H) 6.52(s, 1H); 6.72(s, 1H); 7.61(s, 1H) |
| 25 | H | OMe | O—Al | H | 1.3 | 10 | 3.0 | 3 | 0.72 (58.5) | j-3 | 2.53–2.83(m, 2H); 3.60–3.96(m, 2H) 3.90(s, 3H); 4.57–4.76(m, 2H) 5.20–5.58(m, 2H); 5.87–6.37(m, 1H) 6.48(s, 1H); 6.71(s, 1H); 7.12(s, 1H) |
| 26 | H | OMe | O—Bz | H | 3.86 | 35 | 10.9 | 2.5 | 1.22 (30.3) | j-4 | 2.53–2.76(m, 2H); 3.63–3.87(m, 2H) 3.90(s, 3H); 5.16(s, 2H); 5.39(s, 1H) 5.70(s, 1H); 7.25–7.53(m, 5H); 7.57(s, 1H) |
| 27 | H | O—Al | H | H | 0.88 | 15 | 2.2 | 2 | 0.37 (44.8) | j-5 | 2.60–2.87(m, 2H); 3.67–3.93(m, 2H) 4.50–4.73(m, 2H); 5.20–5.60(m, 2H) 5.80–6.33(m, 1H); 6.53(s, 1H) 6.77(s, 1H); 6.73–6.95(m, 1H) 7.97(d, j=9Hz, 1H) |
| 28 | H | OMe | H | H | 2.15 | 30 | 6.0 | 2 | 0.43 (21.5) | j-6 | 2.58–2.86(m, 2H); 3.65–3.96(m, 2H) 3.84(s, 3H); 6.51(s, 1H); 6.65(s, 1H) 6.67–6.96(m, 1H) 7.95(d, j=9Hz, 1H) |
| 29 | H | $OCH_2CF_3$ | OMe | H | 2.79 | 19 | 5.8 | 3 | 1.19 (44.9) | j-7 | 2.65(t, 2H); 3.79(t, 2H); 3.91(s, 3H) 4.43(q, 2H); 6.51(s, 1H); 6.82, 7.67(s, s, 1H, 1H) |
| 30 | H | $OCH_2CF_3$ | $OCH_2CF_3$ | H | 1.25 | 7 | 2.2 | 3 | 0.23 (19.6) | j-8 | 2.68(t, 2H); 3.80(t, 2H); 4.38, 4.43, (q, q, 2H, 2H); 6.49(s, 1H) 6.84, 7.78, (s, s, 1H, 1H) |

(No. 2)

TABLE 10-continued

| Ref. No. | R¹ | R² | R³ | R⁴ | Compd. (i) g | xylene (ml) | POCl₃ (ml) | Reaction Time (hr) | Yield (g) (%) | Compd. (j) No. | NMR (CDCl₃), Elemental Analysis M.P. |
|---|---|---|---|---|---|---|---|---|---|---|---|
| 31 | H | OCH₃ | H | OCH₃ | 7.50 | 90 | 18.6 | 6.0 | 4.44 (63.2) | j-9 | 2.53–2.76(m, 2H); 3.64–3.83(m, 2H)3.85(s, 3H); 6.40(s, 2H); 7.42(s, 1H) |
| 32 | H | O—i-Pro | H | H | 2.6 | 30 | 6.5 | 4.0 | 0.57 (23.4) | j-10 | 1.30(s, 3H); 1.38(s, 3H) 2.65–2.83(m, 2H); 3.63–3.91(m, 2H)4.43–4,80(m, 1H); 6.50(s, 1H)6.63–6.90(m, 2H); 7.92(d, j=7Hz, 1H) |
| 33 | H | OCH₃ | OCH₂C≡CH | H | 0.706 | 5.5 | 1.66 | 3 | 0.41 (61.5) | j-11 | 2.51(t, 1H); 2.67(t, 2H) 3.78(t, 2H); 3.90(s, 3H) 4.76(d, 2H); 6.50(s, 1H) 6.73(s, 1H); 7.79(s, 1H) |
| 34 | H | O—CH₂—◁ | OMe | H | 2.2 | 30 | 4.8 | 5.0 | 0.46 (22.1) | j-12 | (for C₁₅H₁₇NCl₂O) Calcd. (%): C, 57.34: H, 5.45; N, 4.46; Cl, 22.57 Found (%): C, 57.25; H, 5.47; N, 4.54; Cl, 22,42 m.p.: 99–101° C. |

EXPERIMENT

Antisecretory effect in a rat perfused stomach

Jcl-SD rats (body weight: 300 g) were fasted for 24 hr. prior to the test. Rats were anesthetized with urethane, and the trachea and jugular vein were cannulated. The abdomen was incised along the median line. Respective perfusion cannulae were inserted into the antrum of stomach and the esophagus and fixed there. A warm physiological brine (37° C.) was perfused through the esophagus cannula at the rate of 1 ml/min., and the gastric effluent was collected at a constant interval through the antrum cannula. The perfusate was titrated with 0.01N NaOH to determine the acid secretion. Acid secretion was continuously stimulated by intravenous infusion of histamine.2HCl (3 mg/kg/hr) through the jugular vein cannula. The test compounds were administered intraperitoneally 90 min. after the histamine and the infusate was further collected for 90 min. for titration as described above to determine the maximal suppression of acid secretion.

Test Compound

Compound No. used herein corresponds to the number of Examples in which the compounds was prepared.

Evaluation

The percent suppression in acid secretion (%) was calculated from the acid secretion 90 min. after the histamine 2HCl infusion and the acid secretion at the maximal suppression.

| Test Compd. No. | Results Dose (mg/kg) | Rate of Suppression of Acid Secretion (%) |
|---|---|---|
| Ia - 6 | 3 | 88 |
| Ic - 1 | 3 | 92 |
| Ic - 10 | 10 | 83 |
| Ic - 11 | 10 | 86 |
| Ic - 13 | 10 | 93 |
| Ic - 15 | 10 | 83 |
| Ic - 16 | 10 | 100 |
| Id - 6 | 10 | 100 |
| Id - 7 | 10 | 100 |
| Id - 10 | 10 | 100 |
| Control* | 10 | 48 |

*2-[(1-isoquinolin-1-yl)methylsulfinyl]-5-methoxybenzimidazole disclosed in British Pat. 2134523-A

What we claim is:

1. A compound of the formula:

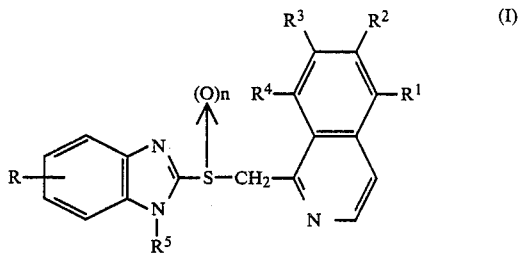

(wherein R is hydrogen, hydroxy, methoxy, acetoxy, acetoxymethyl or trifluoromethyl;

R¹, R², R³ and R⁴ each is hydrogen, hydroxy, C₁–C₅ alkoxy which may be substituted by C₃–C₆ cycloalkyl or one or more halogens, acetoxy, propynyloxy, allyloxy or benzyloxy; or R² and R³ taken together form methylenedioxy;

R⁵ is hydrogen, hydroxymethyl, C₂–C₄ alkoxycarbonyl, C₂–C₅ acyloxymethyl or phthalidyl; and n is 0 or 1 except for the case in which R is methoxy and R¹, R², R³, R⁴ and R⁵ each is hydrogen) or its pharmaceutically acceptable acid addition salt.

2. The compound according to claim 1, namely 2-[(6-methoxyisoquinolin-1-yl)methylsulfinyl]benzimidazole.

3. A pharmaceutical composition comprising a pharmacologically effective amount of a compound according to claim 1 and a pharmaceutically acceptable carrier, diluent and/or excipient.

4. A method of treating a patient suffering from digestive ulcer which comprises administering to the patient a pharmaceutical composition according to claim 3.

5. The compound according to claim 1, wherein C₁–C₅ alkoxy is selected from the group consisting of methoxy, ethoxy, n-propoxy, iso-propoxy, n-butoxy, iso-butoxy, sec-butoxy, tert-butoxy, n-pentyloxy, iso-pentyloxy, sec-pentyloxy, neo-pentyloxy, and tert-pentyloxy.

6. The compound according to claim 1, wherein $C_3$–$C_6$ cycloalkyl is selected from the group consisting of cyclopropyl, cyclopentyl and cyclohexyl.

7. The compound according to claim 1, wherein $C_2$–$C_4$ alkoxycarbonyl is selected from the group consisting of ethoxycarbonyl, propoxycarbonyl, butoxycarbonyl and isobutoxycarbonyl.

8. The compound according to claim 1, wherein $C_2$–$C_5$ acyloxymethyl is selected from the group consisting of alkanoyloxymethyl and alkoxycarbonyloxymethyl.

9. The compound according to claim 8, wherein alkanoyloxymethyl is selected from the group consisting of acetoxymethyl, propionyloxymethyl, butyryloxymethyl, pivaloyloxymethyl and valeryloxymethyl.

10. The compound according to claim 9, wherein alkoxycarbonyloxymethyl is selected from the group consisting of ethoxycarbonyloxymethyl, propoxycarbonyloxymethyl and butoxycarbonyloxymethyl.

11. A pharmacuetically acceptable acid addition salt of the compound of claim 1.

12. The pharmaceutically acceptable acid addition salt according to claim 11, wherein the acid is an inorganic acid selected from the group consisting of hydrochloric acid, sulfuric acid, phosphoric acid and nitric acid.

13. The pharmaceutically acceptable acid addition salt according to claim 11, wherein the acid is an organic acid selected from the group consisting of acetic acid, maleic acid, malic acid, citric acid, lactic acid, succinic acid and methanesulfonic acid.

14. The composition according to claim 3, comprising 0.1 to 95% by weight of said compound.

15. The composition according to claim 3, wherein said compounds are formulated as tablets, capsules, pills, granules, injections, suppositories and syrups.

16. The method of claim 4, wherein the compounds are administered enterally or parenterally to the patient.

17. The method of claim 4, wherein the dosage of the compound is 0.1 to 500 mg/day when orally administered.

18. The method of claim 4, wherein the dosage of the compound is 0.1 to 300 mg/day when administered by injection.

19. A compound of the formula:

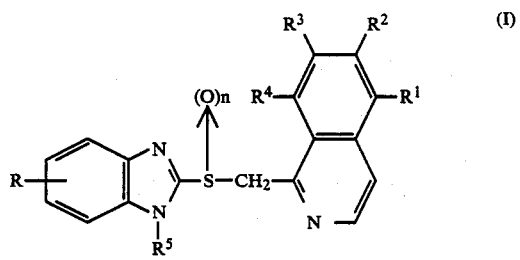

(wherein R is hydrogen, hydroxy, methoxy, acetoxy, actoxymethyl or trifluoromethyl;

$R^1$, $R^2$, $R^3$ and $R^4$ each is hydrogen, hydroxy, $C_1$–$C_5$ alkoxy, acetoxy, propynyloxy, allyloxy or benzyloxy; or $R^2$ and $R^3$ taken together form methylenedioxy;

$R^5$ is hydrogen, hydroxymethyl, $C_2$–$C_4$ alkoxycarbonyl, $C_2$–$C_5$ acyloxymethyl or phthalidyl; and n is 0 or 1 except for the case in which R is methoxy and $R^1$, $R^2$, $R^3$, $R^4$ and $R^5$ each is hydrogen)

or its pharmaceutically acceptable acid addition salt.

20. A pharmaceutical composition comprising a pharmacologically effective amount of a compound according to claim 19 and a pharmaceutically acceptable carrier, diluent and/or excipient.

21. A method of treating a patient suffering from a digestive ulcer which comprises administering to the patient a pharmaceutical composition according to claim 20.

* * * * *